US006271402B1

(12) United States Patent
Singh et al.

(10) Patent No.: US 6,271,402 B1
(45) Date of Patent: Aug. 7, 2001

(54) HIV INTEGRASE INHIBITORS

(75) Inventors: Sheo Bux Singh, Edison; Deborah L. Zink, Manalapan, both of NJ (US); Daria Jean Hazuda; Peter J. Felock, both of Doyleston, PA (US); Anne W. Dombrowski, East Brunswick, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/459,840

(22) Filed: Dec. 13, 1999

Related U.S. Application Data

(60) Provisional application No. 60/112,168, filed on Dec. 14, 1998.

(51) Int. Cl.$^7$ .................. C07J 9/00; C07J 71/00
(52) U.S. Cl. .................. 552/541; 540/61
(58) Field of Search .................. 552/541, 544, 552/546

(56) References Cited

U.S. PATENT DOCUMENTS

| | | | |
|---|---|---|---|
| 4,871,727 | * 10/1989 | Burg et al. | 514/179 |
| 5,292,773 | * 3/1994 | Hirsch et al. | 514/554 |
| 5,716,777 | 2/1998 | Byskov et al. | |

FOREIGN PATENT DOCUMENTS

| | | |
|---|---|---|
| 97/00884 | * 1/1997 | (WO) . |
| WO98/31371 | 7/1998 | (WO) . |

OTHER PUBLICATIONS

Yagen et al., J. Chem. Soc., Perkin Trans. I, pp. 2914–2917, 1980.*

O'Donnell, et al., "Molecular systematics and phylogeography of the Gibberella fujikuroi species complex", Mycologia, 90 (3), pp 465–493, 1998.

Nicklaus, et al., "HIV–1 Integrase Pharmacophore: Discovery of Inhibitors through Three–Dimensional Database Searching", J. Med. Chem., 40, pp 920–929, 1997.

Hong, et al., "Discovery of HIV–1 Integrase Inhibitors by Pharmacophore Searching", J. Med. Chem., 40, pp.930–936, 1997.

Zhao, et al., "Hydrazide–Containing Inhibitors of HIV–1 Integrase", J.Med.Chem., 40, pp.937–941, 1997.

Neamati, et al., "Depsides and Depsidones as Inhibitors of HIV–1 Integrase: Discovery of Novel Inhibitors through 3D Database Searching", J. Med. Chem., 40, pp. 942–951, 1997.

Zhao, et al., "Arylamide Inhibitors of HIV–1 Integrase", J.Med. Chem., 40, pp. 1186–1194, 1997.

Mazumder, et al, "Curcumin Analogs with Altered Potencies against HIV–1 Integrase as Probes for Biochemical Mechanisms of Drug Action", J. Med. Chem., 40, pp. 3057–3063, 1997.

Lubkowksi, et al, "Structure of the catalytic domain of avian sarcoma virus integrase with a bound HIV–1 integrase–targeted inhibitor", Proc. Natl. Acad. Sci. USA, 95, pp.4831–4836, Apr. 1998.

Neamati, et al, "Thiazolothiazepine Inhibitors of HIV–1 Integrase", Journal of Medicinal Chemistry, vol. 42, pp. 3334–3341, 1999.

Reddy, et al, "Lamellarin a 20–Sulfate, an Inhibitor of HIV–1 Integrase Active against HIV–1 Virus in Cell Culture", J. Med. Chem., 42, pp. 1901–1907, 1999.

Lin, et al, "Chicoric Acid Analogues as HIV–1 Integrase Inhibitors", J. Med. Chem., 42, pp. 1401–1414, 1999.

Artico, et al, "Geometrically and Conformationally Restrained Cinnamoyl Compounds as Inhibitors or HIV–1 Integrase: Synthesis, Biological Evaluation, and Molecular Modeling", J. Med. Chem., 41, pp. 3948–3960, 1998.

Neamati, et al. "Salicylhydrazine–Containing Inhibitors of HIV–1 Integrase: Implication for a Selective Chelation in the Integrase Active Site", J. Med. Chem., 41, pp. 3202–3209, 1998.

Mekouar, et al, "Styrylquinoline Derivatives: A New Class of Potent HIV–1 Integrase Inhibitors That Block HIV–1 Replication in CEM Cells", J. Med. Chem., 41, 2846–2857, 1998.

Toh, H. et al, "Close structural resemblance between putative polymerase of a Drosophila transposable genetic element 17.6 and pol gene product of Moloney murine Leukaemia virus", The EMBO Journal, vol. 40 No 5 pp. 1267–1272, 1985.

(List continued on next page.)

Primary Examiner—Barbara P. Badio
(74) Attorney, Agent, or Firm—Kenneth R. Walton; Melvin Winokur

(57) ABSTRACT

Compound of formula I:

(I)

[Structure of steroid-like compound with substituents $R^1$, $R^2$, $R^3$, $R^4$, $R^5$, $R^6$, $R^7$ and position labeled $a$]

wherein the R groups are as defined by the specification. The compounds are useful in the inhibition of HIV integrase, the treatment of infection of HIV and treatment of AIDS.

12 Claims, No Drawings

OTHER PUBLICATIONS

LaFemina, et al., "Inhibition of Human Immunodeficiency Virus Integrase by Bis–Catechols", Antimicrobial Agents & Chemotherapy, vol. 39, No. 2, pp. 320–324, Feb. 1995.

Power, M.D., et al., "Nucleotide Sequence of SRV–1, a Type D Simian Acquired Immune Deficiency Syndrome Retrovirus", Science, 231, 1567–1572 (1986).

Ratner, L. et al., "Complete nucleotide sequence of the AIDS virus, HTLV–III", Nature, 313–, 277–284 (1985).

Zhao et al., "Hydrazide–Containing Inhibitors of HIV–1 Integrase", J.Med. Chem., vol. 40, pp. 937–941 (1997).

Pearl, L.H. et al., "A Structural model for the retroviral proteases", Nature, vol. 329, 351–354 (1987).

Brill, et al., "Novel Triterpene Sulfates from Fusarium compactum Using a Rhinovirus 3C Protease Inhibitor Screen", J. Antibiotics, 49(6):541–546 (1996).

* cited by examiner

HIV INTEGRASE INHIBITORS

CROSS-REFERENCE TO RELATED APPLICATIONS

This patent application claims the benefit of United States provisional patent application Ser. No. 60/112,168, filed Dec. 14, 1998, the disclosure of which is hereby incorporated by reference in its entirety.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, e.g., azidothymidine or AZT. Applicants demonstrate that the compounds of this invention are inhibitors of HIV integrase and inhibitors of HIV replication. The applicants additionally demonstrate that inhibition of integrase in vitro and HIV replication in cells is a direct result of inhibiting the strand transfer reaction catalyzed by the recombinant integrase in vitro and integrase as a component of the preintegration complex in HIV infected cells. The particular advantage of the present invention is highly specific inhibition of HIV integrase and HIV replication. The compounds of the present invention inhibit integrases of closely related lentiviruses such as HIV 2 and SIV, but not integrases from more distantly related retroviruses, for example RSV. These compounds do not inhibit binding or catalysis of other nucleic acid binding proteins, including enzymatic reactions such as those catalyzed by HIV reverse transcriptase, HIV Rnase H, Influenza transcriptase, Hepatitis C polymerase, Yeast DNA polymerase, DNase I, Eco RI endonuclease, or mammalian polymerase II.

Zhao et al., (J. Med Chem. vol. 40, pp. 937–941 and 1186–1194 (1997)) describe hydrazide and arylamide FUV integrase inhibitors. Bis-catechols useful for inhibiting HIV integrase are described in LaFemina et al. (Antimicrobial Agents & Chemotherapy, vol. 39, no. 2, pp. 320–324, February 1995).

U.S. Pat. No. 4,871,727 to Burg et al. describes anti-inflammatory and degenerative compounds isolated from the soil microorganism ATCC 20858 of structural formula A below:

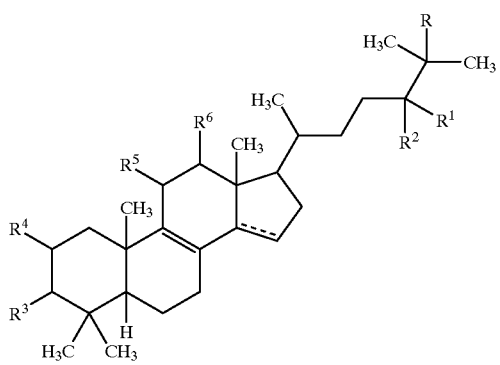

(A)

wherein:

R is OH or H;

$R^1$ and $R^2$ together form $=CH_2$ or $—CH_2O—$;

$R^3$ is H, OH, $HSO_3O$, $HOCOCH_2CH_2CO_2$;

$R^4$ is OH, $HOC_{15}H_{30}CO_2$, AcO or is H except that when $R^4$ is H, the double bond in the cyclopentane ring is absent;

$R^5$ is O=, OH, AcO; and $R^6$ is OH or $—O—C(O)CH_3$.

Brill et al. (J. Antibiotics, 49(6): 541–546 (1996)), describe particular triterpene sulfates from *Fusarium compactum*.

PCT publication WO 98/31371 (Application No. PCT/US98/00766) describe the use of androst-5-ene-3O-ol-7,17 dione and metabolizable precursors thereof, such as androst-5-ene-3β-acetoxy-7,17-dione, for the treatment of HIV-related weight loss, HIV-related cachexia and HIV-related wasting syndrome.

Applicants have discovered that certain natural product compounds derived from Fusarium sp. MF6381 (ATCC 74469) and derivatives thereof are potent inhibitors of HIV integrase. These compounds are useful for the treatment of AIDS or HIV infections.

BRIEF DESCRIPTION OF THE INVENTION

Compounds of formula I, as herein defined, are disclosed. These compounds are useful in the inhibition of HIV integrase, the prevention of infection by HIV, the treatment of infection by HIV and in the treatment of AIDS and/or ARC, either as compounds, pharmaceutically acceptable salts or hydrates (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

Further, the culture Fusarium sp., MF6381 (ATCC 74469) is also disclosed, as well as processes for making compounds of structural formula I employing the culture Fusarium sp., MF6381 (ATCC 74469).

DETAILED DESCRIPTION OF THE INVENTION

This invention is concerned with compounds of formula I, combinations thereof, or pharmaceutically acceptable salts thereof, in the inhibition of HIV integrase, the prevention or treatment of infection by mV and in the treatment of the resulting acquired immune deficiency syndrome (AIDS). Compounds of formula I are defined as follows:

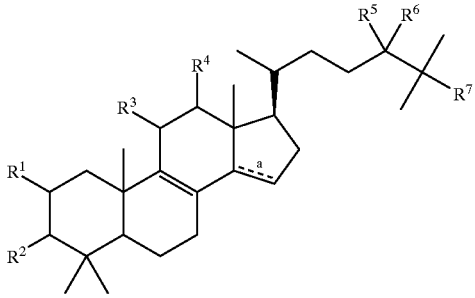

(I)

wherein:
"a" is selected from a single bond or a double bond;
$R^1$ is selected from:
 (a) —OH,
 (b) —OC(O)CH$_3$,
 (c) —OC(O)CH$_2$C(CH$_3$)(OH)CH$_2$CO$_2$H,
 (d) —OC(O)CH$_2$C(CH$_3$)(OH)CH$_2$CO$_2$CH$_3$,
 (e) —OC(O)(CH$_2$)$_2$CO$_2$H,
 (f) —OC(O)(CH$_2$)$_2$CO$_2$CH$_3$,
 (g) —OC(O)(CH$_2$)$_2$CONHOH,
 (h) —OCH$_2$OCH$_3$,
 (i) —OC(O)C$_6$H$_5$,
 (j) —OC(O)CH$_2$NH—C(O)OC(CH$_3$)$_3$,
 (k) —OSO$_2$CH$_3$,
 (l) —OC(O)CH$_2$NH$_2$,
 (m) —OC(O)—(CH$_2$)$_{15}$—OH, and
 (n) H;
$R^2$ is selected from:
 (a) —OH,
 (b) —OC(O)CH$_3$,
 (c) =O,
 (d) —OC(O)(CH$_2$)$_2$CO$_2$H,
 (e) —OC(O)(CH$_2$)$_2$CO$_2$CH$_3$,
 (f) —OC(O)(CH$_2$)$_2$CONHOH,
 (g) —OCH$_2$OCH$_3$,
 (h) —OC(O)C$_6$H$_5$,
 (i) —OC(O)CH$_2$NHC(O)OC(CH$_3$)$_3$,
 (j) —OSO$_2$CH$_3$,
 (k) —OSO$_2$OH, and
 (l) —OC(O)CH$_2$NH$_2$;
or $R^1$ and $R^2$ are joined to form:

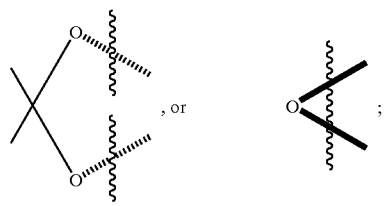

$R^3$ is selected from:
 (a) —H,
 (b) —OH, and
 (c) —OC(O)CH$_3$;
$R^4$ is selected from:
 (a) —H,
 (b) —OH, and
 (c) —OC(O)CH$_3$;
$R^5$ and $R^6$ are independently selected from:
 (a) —H,
 (b) —OH, and
 (c) —CH$_3$,
 or together form:
 (c) =CH$_2$, or
 (d) —CH$_2$O—;
$R^7$ is selected from:
 (a) H, and
 (b) OH;
or a pharmaceutically acceptable salt thereof.

In one class of compounds of the present invention, $R^1$ is selected from:
 (a) —OH,
 (b) —OC(O)CH$_3$,
 (c) —OC(O)CH$_2$C(CH$_3$)(OH)CH$_2$CO$_2$H,
 (d) —OC(O)CH$_2$C(CH$_3$)(OH)CH$_2$CO$_2$CH$_3$,
 (e) —OC(O)(CH$_2$)$_2$CO$_2$H,
 (f) —OC(O)(CH$_2$)$_2$CO$_2$CH$_3$,
 (g) —OC(O)(CH$_2$)$_2$CONHOH,
 (h) —OCH$_2$OCH$_3$,
 (i) —OC(O)C$_6$H$_5$,
 (j) —OC(O)CH$_2$NH—C(O)OC(CH$_3$)$_3$,
 (k) —OSO$_2$CH$_3$,
 (l) —OC(O)CH$_2$NH$_2$,
 (m) —OC(O)—(CH$_2$)$_{15}$—OH, and
 (n) H.

In a subclass of compounds of the present invention, $R^1$ is selected from:
 (a) —OH,
 (b) —OC(O)CH$_2$C(CH$_3$)(OH)CH$_2$CO$_2$H,
 (c) —OC(O)CH$_2$C(CH$_3$)(OH)CH$_2$CO$_2$CH$_3$,
 (d) —OC(O)(CH$_2$)$_2$CO$_2$H,
 (e) —OC(O)(CH$_2$)$_2$CONHOH,
 (f) —OC(O)CH$_2$NH$_2$, and
 (g) —OC(O)—(CH$_2$)$_{15}$—OH.

In one class of compounds of the present invention, $R^2$ is selected from:
 (a) —OH,
 (b) —OC(O)CH$_3$,
 (c) =O,
 (d) —OC(O)(CH$_2$)$_2$CO$_2$H,
 (e) —OC(O)(CH$_2$)$_2$CO$_2$CH$_3$,
 (f) —OCH$_2$OCH$_3$,
 (g) —OC(O)C$_6$H$_5$,
 (h) —OC(O)CH$_2$NHC(O)OC(CH$_3$)$_3$,
 (i) —OSO$_2$OH, and
 (j) —OC(O)CH$_2$NH$_2$.

In a subclass of compounds of the present invention, $R^2$ is selected from:
 (a) —OH,
 (b) =O,
 (c) —OC(O)(CH$_2$)$_2$CO$_2$H,
 (d) —OSO$_2$OH, and
 (e) —OC(O)CH$_2$NH$_2$.

In one class of compounds of the present invention, $R^4$ is —OC(O)CH$_3$.

In another class of compounds of the present invention, $R^5$ and $R^6$ independently are selected from:

(a) —H, and (b) —OH, or together form:

(c) =CH$_2$, or (d) —CH$_2$O—.

In still another class of compounds of the present invention, R$^7$ is hydrogen.

Also included within the present invention are pharmaceutical compositions useful for inhibiting HIV integrase, comprising an effective amount of a compound of this invention, and a pharmaceutically acceptable carrier. Pharmaceutical compositions useful for treating infection by HIV, or for treating AIDS or ARC, are also encompassed by the present invention, as well as a method of inhibiting HIV integrase, and a method of treating infection by HIV, or of treating AIDS or ARC. Additionally, the present invention is directed to a pharmaceutical composition comprising a therapeutically effective amount of a compound of the present invention in combination with a therapeutically effective amount of an AIDS treatment agent selected from:

(1) an AIDS antiviral agent, (2) an anti-infective agent, and (3) an immunomodulator.

The compounds of the present invention may have asymmetric centers and may occur, except when specifically noted, as mixtures of stereoisomers or as individual diastereomers, or enantiomers, with all isomeric forms being included in the present invention.

Some of the compounds of the present invention are made by chemical modification of Compound A:

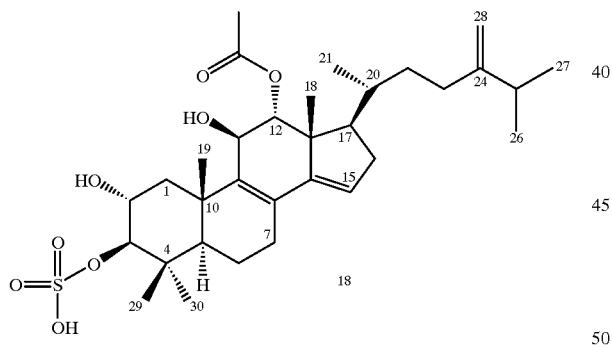

A

U.S. Pat. No. 4,871,727 describes the production of Compound A by cultivation from a soil microorganism, ATCC 20858. Compound A is therein described as an elastase inhibitor.

U.S. Pat. No. 4,871,727 also describes the production of the following compounds by cultivation from the soil microorganism ATCC 20858, or alternatively by cultivation from the soil microorganism ATCC 20858 followed by chemical modification:

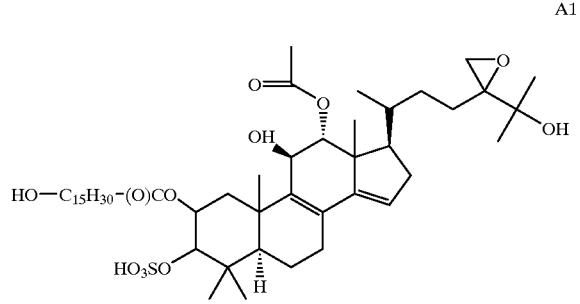

A1

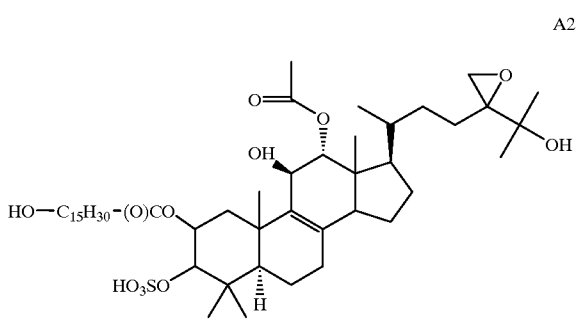

A2

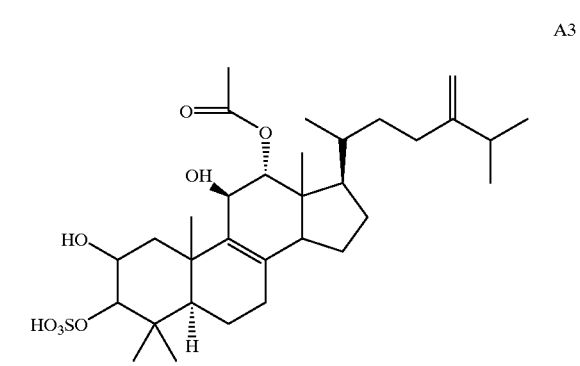

A3

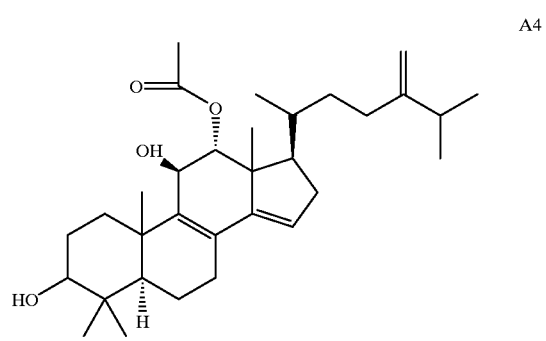

A4

A5

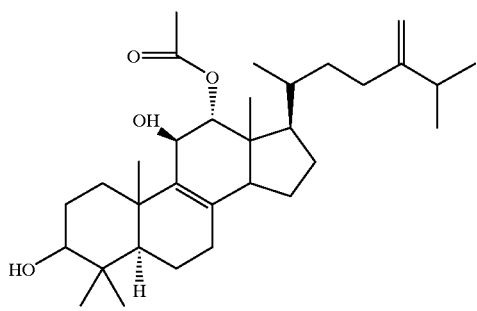

B

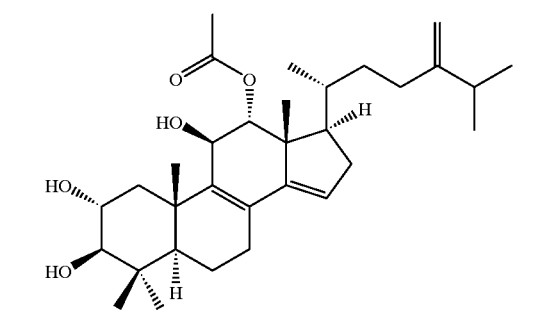

J

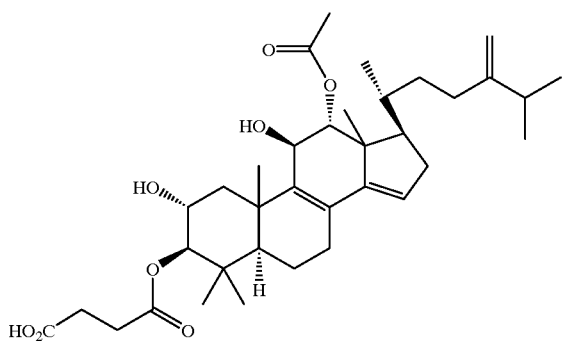

O

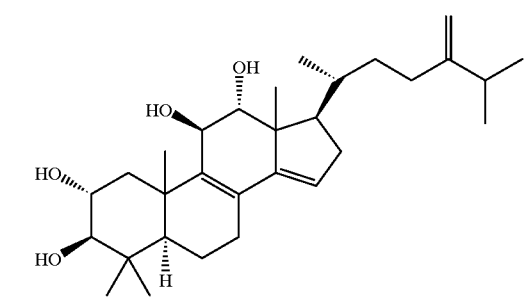

This invention also discloses the culture MF6381 (ATCC 74469) identified as Fusarium sp.

In addition, compounds of the present invention, including Compound A, may be prepared by fermentation of the culture MF6381, ATCC 74469.

Compounds of the present invention may be prepared by chemical modification of Compound A, or Compound B.

The present invention also relates to the preparation of compounds of structural formula I comprising:
(a) fermenting a culture of MF6381 (ATCC 74469), Fusarium sp. or a mutant thereof to produce a fermentation broth,
(b) extracting the fermentation broth with an organic solvent,
(c) isolating the compounds of structural formula I.
Alternatively, an additional step may be performed:
(d) chemically modifying the isolated compound of formula I.

The compounds of structural formula I are preferably isolated by partitioning the fermentation extract between the organic solvent and water, followed by size exclusion chromatography and normal or reverse-phase chromatography.

When any variable (e.g., $R^1$, $R^2$, etc.) occurs more than one time in any constituent or in formula I, its definition on each occurrence is independent of its definition at every other occurrence. Also, combinations of substituents and/or variables are permissible only if such combinations result in stable compounds.

The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus, the compounds of this invention are commercial products to be sold for these purposes.

The present invention also provides for the use of a compound of structural formula (I) to make a pharmaceutical composition useful for inhibiting HIV integrase and in the treatment of AIDS or ARC.

Applicants have discovered that compounds of structural formula (I), are useful for inhibiting HIV integrase. The compounds of formula (I) are prepared by an aerobic fermentation.

ATCC Deposit of MF6381 (ATCC 74469), Identified as Fusarium, sp.

Before the U.S. filing date of the present application, a sample of MF6381 (ATCC 74469), Fusarium sp., was deposited at the American Type Culture Collection (ATCC), 10801 University Boulevard, Manassas, Va. 20110-2209, United States of America under the terms of the Budapest Treaty. The culture access designation is ATCC 74469. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.

General Characteristics and Description of MF6381 (ATCC 74469) Fusarium sp.

MF6381 was isolated from soil collected in Africa.

In the following description, MF6381 was edge inoculated with a 5 mm diameter plug on 2,100 mm petri dishes for each the following growth media. All cultures were incubated for 10 days at 25° C. and 67% relative humidity in 12 hr photoperiod in fluorescent light unless otherwise indicated. In addition, all capitalized color names are from Ridgway, *Color Standards and Nomenclature,* (Published by author, Washington D.C., 1912) 43p.+53 pl.

On oatmeal agar (Difco) colony mat attaining a diameter of 55 mm. Culture mat thickly woolly, forming distinct tufts. Area of the inoculation point yellow (Buff Yellow, Pinard Yellow), at colony center and margin light red to pink (Venetian Pink, Chatenay Pink, Alizarine Pink). Margin white, entire. Reverse brown (Apricot Buff). Exudate and soluble pigment absent.

On potato-dextrose agar (Difco), colony mat attaining a diameter of 67 mm. Culture mat cottony to flat, consistent throughout. Area of the inoculation point yellow (Antimony Yellow, Ochraceous Buff). Area of colony center pink (Flesh Pink, Chatenay Pink, Flesh Color). Margin light brown (Salmon-Buff), entire. Reverse dark brown at inoculation point (Hazel, Cinnamon-Rufous) to light brown near margin (Salmon-Buff). Exudate and soluble pigment absent.

On cornmeal agar (Difco), colony mat attaining a diameter of 70 mm. Colony mat cottony, forming sparse, white tufts of mycelium, otherwise hyaline. Margin entire, hyaline. Exudate, reverse and soluble pigment absent.

On YME agar (malt extract, 10.0 g; yeast extract, 4.0 g; dextrose, 4.0 g; agar, 20.0 g, distilled water, 1 L) attaining a diameter of 67 mm. Culture mat cottony, at colony center hyphae aggregated into tufts. Culture mat at inoculation point light yellow (Light Buff, Cream Color) and light pink near margin (Flesh Pink, Chatenay Pink). Reverse, exudate and soluble pigment absent. At 37° C., in the dark and no humidity control, culture mat attaining a diameter of 10 mm. Culture mat mostly appressed to slight cottony, mostly with light brown sections (Pale Ochraceous-Buff, Warm Buff), sulcate. Reverse, exudate and soluble pigment absent.

Microscopic: Hyphae hyaline, usually 2–3 μm wide, up to 4 μm wide. No conidiophores observed. Conidia, hyaline, elliptical, 5–6×2–3 μm. Large swollen cells, 10 μm diameter, singly or in clusters.

Although MF6381 is easily placed into the genus Fusarium (Ascomycotina, Hypocreales) by typical growth characteristics observed in plate cultures and certain microscopic features, it is difficult to speciate this fungus without additional characteristics to distinguish it from the numerous described species of Fusarium.

For a more complete description, another characteristic of MF6381 included below is the ribosomal DNA sequence of the Internal Transcribed Spacer (ITS) region using the primers ITS1 and ITS4. The primers and the techniques used to recover the sequence are described in White, et.al., Amplification and direct sequencing of fungal ribosomal RNA genes for phylogenetics, in PCR Protocols: a *Guide to Methods and Applications* 315–322 (Innis, M. A., et al., eds., Academic Press 1990).

By comparing the sequence from MF6381 using a BLAST search of GenBank, it was determined that MF6381 is closely related (99% match of 502 base pairs) to another Fusarium sp. (NRRL 25483, GenBank accession: u61695, NID g3320369), isolated from *Pennisetum typhoideum* collected in Namibia. It has been cited in O'Donnell et al., Molecular systematics and phylogeography of the *Gibberella fujikuroi* species complex, Mycologia 90, 465 (1998).

Sequence from Nuclear ribosomal DNA (rDNA)
Internal Transcribed Spacer (ITS) region using -continued
primers ITS1/ITS4 (SEQ. ID. NO.:1)

TTTACAACTCCCAAACCCCTGTGAACATACCTATACGTTGCCTCGGC

GGATCAGCCCGCGCCCCGTAAAACGGGACGGCCCGCCGCAGGACCC

ATAAACCCTGAATTTTATTGTAACTTCTGAGTTTAAAAAACAAATAA

ATCAAAACTTTCAACAACGGATCTCTTGGTTCTGGCATCGATGAAGA

ACGCAGCAAAATGCGATAAGTAATGTGAATTGCAGAATTCAGTGAA

TCATCGAATCTTTGAACGCACATTGCGCCCGCCAGTATTCTGGCGGG

CATGCCTGTTCGAGCGTCATTTCAACCCTCAAGCCCCCGGGTTTGGT

GTTGGGGATCGGGCTGCGGTTCTACCGCGTCCCGGCCCCGAAATCT

AGTGGCGGTCTCGCTGCAGCCTCCATTGCGTAGTAGCTAACACCTCG

CAACTGGAACGCGGCGCGGCCAAGCCGTTAAACCCCCAACTTCTGA

ATGTTGACCTCGGATCAGGTAGGAATACCCGCTGAA

In general, MF6381 (ATCC 74469) is strain cultured on a solid medium, or in an aqueous nutrient medium containing sources of assimilable carbon and nitrogen. For example, the cultures can be grown under submerged aerobic conditions (e.g., shaking culture, submerged culture, etc.) The aqueous medium is preferably maintained at a pH of about 6–8 at the initiation of the fermentation process. The desired pH may be maintained by the choice of nutrient materials which inherently possess buffering properties, or alternatively by the use of a buffer such as morpholinoethanesulfonic acid (MES), morpholino-propanesulfonic acid (MOPS), and the like.

The sources of carbon in the nutrient medium are carbohydrates such as glucose, xylose, galactose, glycerin, starch, sucrose, dextrin, and the like. Other sources which may be included are maltose, rhamnose, raffinose, arabinose, mannose, sodium succinate, and the like.

The sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

Agitation and aeration of the culture mixture may be accomplished in a variety of ways. Agitation may be provided by a propeller or similar mechanical agitation equipment, by revolving or shaking the fermentor or growth flask, by various pumping equipment, or by the passage of sterile air through the medium. Aeration may be effected by passing sterile air through the fermentation mixture.

The fermentation is usually conducted at a temperature between about 20° C. and 30° C., preferably 22–25° C., for a period of about 14–21 days, which may be varied according to fermentation conditions and scales.

As to the conditions for the production of cells in massive amounts, submerged aerobic cultural conditions is one method of culturing the cells. For the production in small amounts, a shaking or surface culture in a flask or bottle is employed. The use of fermentors (tanks) is preferred for the generation of large quantities of materials. Fermentors can be sterilized with the production medium or can be sterilized empty and the medium sent through a continuous sterilizer, which is preferred for very large fermentations (20,000 gallons or larger). Preferably, the pH of the medium is adjusted to about 6–7, generally using acid or base additions, preferably made automatically with a pH electrode and a controller. The parameters for fermenter operation include agitation, aeration, temperature and pressure. Agitation is preferably carried out by mixing the medium with a number of impellers mounted on a rotating agitator shaft located in the midst of the tank. Aeration may be carried out by a variety of means, preferably by bubbling sterile air into the medium, preferably at 0.25 v.v.m. to 1.0 v.v.m. (e.g., airflow=7 liters/minute at a medium volume of 14 liters equals 0.5 v.v.m.) The pressure in the tank would be maintained between 3 psig to 15 psig. Temperature is preferably maintained at between about 20° C. and 30° C., preferably 22–25° C.

When the growth is carried out in large tanks, vegetative forms of the organism for inoculation in the production tanks may be employed in order to avoid growth lag in the process of production. This requires production of a vegetative inoculum of the organism by inoculating a relatively small quantity of culture medium with spores or mycelia of the organism produced in a "slant" and culturing said inoculated medium, also called the "seed medium", and then transferring the cultured vegetative inoculum aseptically to large tanks. The fermentation medium, in which the inoculum is produced, is generally sterilized prior to inoculation. The pH of the medium is generally adjusted to about 6–7 prior to the autoclaving step, generally using acid or base additions, preferably made automatically with a pH electrode and a controller.

Preferred culturing/production media for carrying out the fermentation are those set forth in the Examples.

After growth is completed, the cells are harvested by adding the appropriate solvent, e.g. methylethylketone, to the entire culture medium and cells. If the culture is grown in a liquid fermentation, the growth could be harvested by other conventional methods, e.g., centrifugation and filtration, and then extracted with the appropriate solvent, e.g., methylethylketone, ethyl acetate, methylene chloride and the like.

Preferably, the broth filtrate is diluted with a suitable solvent such as methanol or acetone and the product is recovered on resins such as SP207, HP20, amberchrome and the like.

The product of the present invention can be recovered from the culture medium by conventional means which are commonly used for the recovery of other known substances. The substances produced may be found in either or both the cultured mycelium and broth filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methylene chloride or methanol and the like, pH adjustment, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), crystallization, recrystallization, and the like. A preferred method is extraction of cultured whole broth with methylethylketone, followed by filtration of the extract through filtering aid such as diatomaceous earth. The methylethylketone layer of the filtrate is separated and concentrated to dryness initially by evaporating under reduced pressure followed by lyophilization. The compounds are finally isolated either by solvent partitioning and crystallization or by size exclusion, normal, and or reversed-phase HPLC.

Compounds of formula (I) may be isolated from the aerobic fermentation of a culture of MF6381 (ATCC 74469). A culture of MF6381 (ATCC 74469) is defined as substantially free of its natural soil contaminants and capable of forming compounds of structural formula (I) in recoverable amounts. The culture employed in the present invention should be free from viable contaminating microorganisms deleterious to the production of the compound of structural formula (I). A biologically pure culture of MF6381 (ATCC 74469) may also be employed. The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The terms "administration of" and or "administering a" compound should be understood to mean providing a compound of the invention or a prodrug of a compound of the invention to the individual in need of treatment.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

As used herein, the term "composition" is intended to encompass a product comprising the specified ingredients in the specified amounts, as well as any product which results directly, or indirectly, from combination of the specified ingredients in the specified amounts.

By "pharmaceutically acceptable" it is meant the carrier, diluent or excipient must be compatible with the other ingredients of the formulation and not deleterious to the recipient thereof.

These pharmaceutical compositions may be in the form of orally-administrable suspensions or tablets, nasal sprays, sterile injectible preparations, for example, as sterile injectible aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-initiating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 1 to 1000 mg/kg body weight in divided doses. One preferred dosage range is 0.1 to 200 mg/kg body weight orally in divided doses. Another preferred dosage range is 0.5 to 100 mg/kg body weight orally in divided doses. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of AIDS. For example, the compounds of this invention may be effectively administered, whether at periods of pre-exposure and/or post-exposure, in combination with effective amounts of the AIDS antivirals, imunomodulators, antiinfectives, or vaccines, such as those in the following table.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| 141 W94 | Glaxo Wellcome | HIV infection, AIDS, ARC (protease inhibitor) |
| 1592U89 | Glaxo Wellcome | HIV infection, AIDS, ARC (protease inhibitor) |
| Abacavir (1592U89) | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC |

-continued

| Drug Name | Manufacturer | Indication |
|---|---|---|
| CI-1012 | Warner-Lambert | (protease inhibitor) HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (-)6-Chloro-4(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC |

-continued

| Drug Name | Manufacturer | Indication |
|---|---|---|
| | | (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |
| IMMUNO-MODULATORS | | |
| AS-101 | Wyeth-Ayerst | AIDS |
| Bropirimine | Pharmacia Upjohn | advanced AIDS |
| Acemannan | Carrington Labs; Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |

-continued

| Drug Name | Manufacturer | Indication |
|---|---|---|
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptospoildial diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Megestrol Acetate | Bristol-Myers Squibb | treatment of anorexia assoc. w/AIDS |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide, and is synthesized according to U.S. Pat. No. 5,413,999. Indinavir is generally administered as a sulfate ethanolate salt at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 14IW94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Indinavir is an inhibitor of HIV protease and is N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide, and is synthesized according to U.S. Pat. No. 5,413,999. Indinavir is generally administered as the sulfate ethanolate salt at a dosage of 800 mg three times a day.

The following examples are provided to further illustrate details for the preparation and use of the compounds of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

Abbreviations: Ac represents acetyl; ACN is acetonitrile; BOC and t-BOC are t-butoxycarbonyl; Bn represents benzyl; Bz represents benzoyl; DBU is 1,8-diazabicyclo[5.4.0]

undec-7-ene; DIEA is diisopropylethylamine; DMAP is 4-dimethylaminopyridine; DMF is dimethyl formamide; Fmoc is N-(9-fluorenylmethoxycarbonyl); Et represents ethyl; HPLC is high pressure liquid chromatography; IPA is isopropyl alcohol; MEK is methyl ethyl ketone; Me represent methyl; MOM is methoxymethyl; Ms represents methane sulfonyl; PDA is photodiode array; TFA is trifluoroacetic acid; THF is tetrahydrofuran; TLC is thin layer ($SiO_2$) chromatography.

EXAMPLE 1

Fermentation of MF6381 (ATCC 74469) Using Solid Medium

A. Media

Seed Medium:

| Component | g/L |
|---|---|
| Yeast extract | 4.0 |
| Malt extract | 8.0 |
| Glucose | 4.0 |
| Junlon | 1.5 |

The medium was prepared with distilled water, the pH adjusted to 7.0 prior to sterilization, and was dispensed at 50 mL/250 mL unbaffled Erlenmeyer flask. Cotton closures were used. Sterilization was at 121° C. for 20 minutes.

Production Medium:

1. Solid Portion:

675 cc vermiculite was added to a 2 liter roller bottle which was plugged with latex closure and autoclaved for 60 minutes, plus 30 minutes on the dry cycle.

2. Liquid Portion

| Component | g/L |
|---|---|
| Glycerol | 75.0 |
| Glucose | 10.0 |
| Ardamine pH | 5.0 |
| $(NH_4)_2SO_4$ | 2.0 |
| Soybean meal | 5.0 |
| Tomato paste | 5.0 |
| Sodium citrate | 2.0 | pH to 7.0

The medium was prepared with distilled water, dispensed at 220 mL in 500 mL bottles and sterilized at 121° C. for 20 minutes.

B. Inoculum Preparation

Growth from an agar slant was used to prepare FVMs (frozen vegetative mycelia). A portion of the agar slant was transferred aseptically to seed medium. (The composition of the seed medium is detailed above). The flasks were incubated on a 2-inch throw gyratory shaker, 220 rpm for 2 days at 25° C., 85% relative humidity (rh), to obtain biomass. Portions of the biomass were transferred into sterile vials containing glycerol and frozen (as FVM). These were maintained in a final concentration of 10–15% glycerol at −75° C.

C. Seed Culture

Frozen vials (FVM) were thawed to room temperature and used to inoculate seed cultures, at 1.0 mL per 50 mL seed medium. The cultures were grown on a gyratory shaker (220 rpm) for 2 days at 25° C., 85% rh, until a sufficient amount of biomass was obtained.

D. Production

The composition of the solid substrate fermentation medium is shown above. An aliquot (12 mL) of each grown seed was placed into 220 mL of the liquid portion of the production. This was swirled vigorously to disperse the biomass. The contents were dispensed by pouring into a 2-liter roller culture vessel which contained 675 cubic centimeters of steam-sterilized large-particle vermiculite. The contents of the roller bottle were shaken/mixed to insure homogeneous inoculation and coverage. The roller bottles were incubated horizontally, revolving at approximately 4 rpm on a Wheaton roller apparatus at 22° C., 75% rh for 18 days, to obtain secondary metabolite production in the fermentation medium.

EXAMPLE 2

Fermentation of MF6381 (ATCC 74469) Using Liquid Medium

A. Media

1. KF Seed Medium

| Component | g/L |
|---|---|
| Corn steep powder | 2.5 |
| Tomato paste | 40.0 |
| Oat flour | 10.0 |
| Glucose | 10.0 |
| Trace elements solution | 10.0 mL/L | pH to 6.8 NaOH

| TRACE ELEMENTS SOLUTION | |
|---|---|
| $FeSO_4 \cdot 7H_2O$ | 1.0 |
| $MnSO_4 \cdot H_2O$ | 1.0 |
| $CuCl_2 \cdot 2H_2O$ | 0.025 |
| $CaCl_2 \cdot H_2O$ | 0.1 |
| $H_3BO_3$ | 0.056 |
| $(NH_4)_6Mo_7O_{24} \cdot 4H_2O$ | 0.019 |
| $ZnSO_4 \cdot 7H_2O$ | 0.2 |

Trace elements prepared in 0.6N HCl

The medium was prepared with distilled water, the pH adjusted to 6.8 prior to sterilization, and was dispensed at 50 mL/250 mL unbaffled Erlenmeyer flask. Cotton closures were used. Sterilization was at 121° C. for 20 minutes.

2. Liquid Production Medium

| Component | g/L |
|---|---|
| Glucose | 150.0 |
| Glycerol | 20.0 |
| Yeast extract | 4.0 |
| $NaNO_3$ | 1.0 |
| Monosodium glutamate | 3.0 |
| $Na_2HPO_4$ | 0.5 |
| $MgSO_4 \cdot 7H_2O$ | 1.0 |
| $CaCO_3$ | 8.0 |
| K-elements | 1.0 mL/L |
| pH to 7.0. with NaOH Autoclave 15 min | |
| K-elements | |
| $FeCl_3 \cdot 6H_2O$ | 5.8 |
| $MnSO_4 \cdot H_2O$ | 0.1 |
| $CoCl_2 \cdot 6H_2O$ | 0.02 |
| $CuSO_4 \cdot 5H_2O$ | 0.015 |
| $Na_2MoO_4 \cdot 2H_2O$ | 0.012 |
| $ZnCl_2$ | 0.02 |
| $SnCl_2 \cdot 2H_2O$ | 0.005 |
| $H_3BO_3$ | 0.01 |
| KCl | 0.02 |
| HCl (concentrated) | 2.0 ml/L |

The medium was prepared with distilled water, dispensed at 50 mL per 250 mL flask, and sterilized at 121° C. for 15 minutes.

B. Seed:

Frozen vials (FVM) were thawed to room temperature and used to inoculate KF medium seed cultures, at 1.0 mL per 50 mL seed medium. The cultures were grown on a gyratory shaker (220 rpm) for 2 days at 25° C., 85% rh, until a sufficient amount of biomass was obtained.

C. Production:

The composition of the solid substrate fermentation medium is shown in the table above. An aliquot (1–2 mL) of each grown seed was placed into 50 mL of the liquid production medium in 250 mL flasks. The flasks were incubated at 22° C. for 7–21 days.

EXAMPLE 3
Isolation of A

Compound A

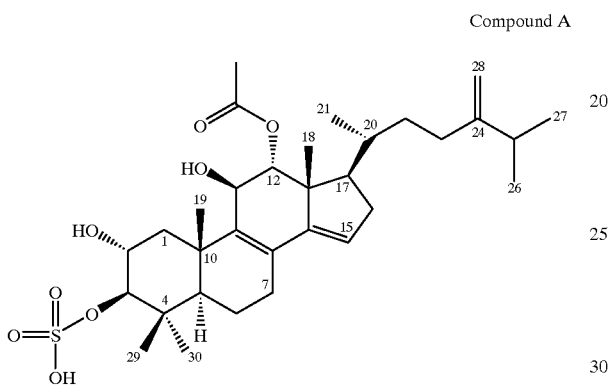

The Fusarium culture grown on vermiculite medium was extracted with 1.2 volume methyl ethyl ketone (MEK) by shaking at a shaker for 30–60 min. Sixty mL of the MEK extract was concentrated to dryness and the residual water was removed by lyophilization to give 180 mg of pale residue. This material was dissolved in 5 mL methanol-methylene chloride (1:1) and was charged on to a 1 L SEPHADEX LH-20 column packed in methanol. Twenty mL each fractions were collected at a flow rate of ~20 mL/min. The compound eluted from 400 mL to 900 mL of the elution volume of methanol. The combined fractions were concentrated to give the title compound as a colorless powder. $^1$H NMR (acetone-$d_6$+10% $CD_3OD$) δ: 5.56 (1H, brs, H-15), 5.04 (1H, brd, J=1.2 HZ, H-12),4.70,4.66 (1H each, brs, H-28), 4.24 (1H, brs, H-11), 3.91 (1H, brdt, J=10, 4 Hz, H-2), 3.82 (1H, d, J=10 Hz, H-3), 2.44 (1H, m, H-16), 2.38 (1H, dd, 12,4 Hz, H-1β), 2.37 (1H, m, H-7α), 2.30 (1H, m, H-7β), 2.23 (1H, hept, J=6.8 Hz, H-25), 2.14 (1H, m, H-23), 2.05 (1H, m, H-16), 2.00 (1H, m, H-17), 1.95 (3H, s, $H_3$-32), 1.91 (1H, m, H-23), 1.77 (1H, m, H-6), 1.69 (1H, m, H-6), 1.68 (1H, m, H-20), 1.58 (1H, m, H-22), 1.31 (3H, s, $H_3$-19), 1.27 (1H, m, H-1α), 1.23 (1H, m, H-5), 1.14 (1H, m, H-22), 1.09 (3H, s, $H_3$-18), 1.08 (3H, s, $H_3$-30), 1.01, 1.00 (6H, d, J=6.8 Hz, $H_3$-26, $H_3$-27), 0.91 (3H, d, J=6.4 Hz, $H_3$-21), 0.87 (3H, s, $H_3$-29); $^{13}$C NMR (acetone-$d_6$+10% $CD_3OD$) δ: 170.70 (C-31), 157.12 (C-24), 148.37 (C-14), 140.00 (C-9), 125.47 (C-8), 120.98 (C-15), 106.71 (C-28), 90.11 (C-3), 78.99 (C-12), 69.14 (C-11), 68.20 (C-2), 51.39 (C-5), 49.80 (C-17), 47.68 (C-13), 44.15 (C-1), 40.49 (C-4), 38.56 (C-10), 35.95 (C-16), 35.30 (C-22), 34.35 (C-25), 34.14 (C-20), 31.62 (C-23), 29.22 (C-30), 27.39 (C-7), 23.37 (C-19), 22.30, 22.15 (C-26, C-27), 21.24 (C-32), 18.92 (C-6), 18.50 (C-21), 17.96 (C-29), 17.10 (C-18); ESIMS: m/z 595 [M+H]$^+$, 593 [M−H]$^−$; EIMS: m/z 436 [M−$H_2SO_4$-AcOH]$^+$.

EXAMPLE 4
Preparation of Compound B from A

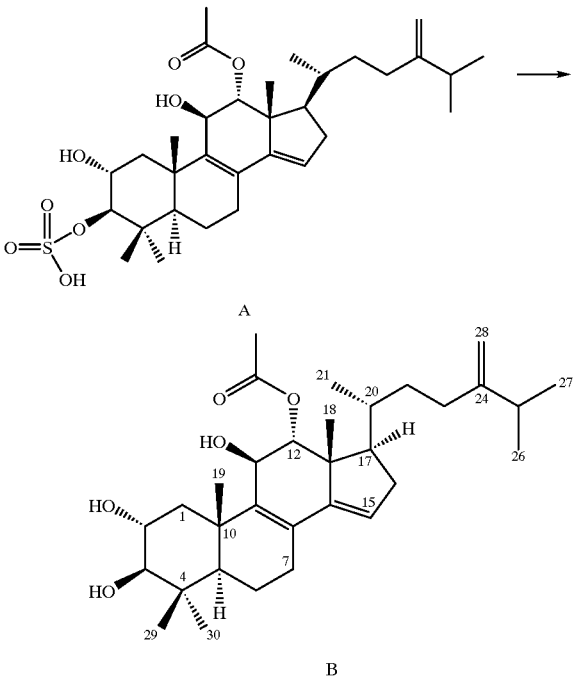

A solution of Compound A L-155,911 (160 mg) in dioxane (16 mL) was heated at 66° C. for 5 min. After addition of sodium bicarbonate (300 mg) the reaction mixture was filtered through a bed of sodium sulfate and washed with ethyl acetate (150 mL). The combined filtrate was washed once each with 50 mL of 10% aqueous sodium bicarbonate and 50 mL water, dried over sodium sulfate, concentrated under reduced pressure and chromatographed over a silica gel column. Elution with 50% ethyl acetate in hexane gave 13 mg of fraction A, 27 mg of fraction B and 72 mg (33%) of Compound B L-155,944 as a gum. Lyophilization of Compound B from acetonitrile-water gave colorless powder. $^1$H NMR (CDCl$_3$) δ: 5.61 (1H, t, J=2.5 Hz, H-15), 4.97 (1H, d, J=2.0 Hz, H-12), 4.73 (1H, brs, H-28), 4.66 (1H, d, J=1.0 Hz, H-28), 4.24 (1H, brs, H-11), 3.81 (1H, ddd, J=11.5, 10,4 Hz, H-2), 3.20 (1H, brs, OH), 3.05 (1H, d, J=9.5 Hz, H-3), 2.45 (2H, m, H-16, H-7β), 2.37 (1H, dd, J=12, 5 Hz, H-1β), 2.32 (1H, dd, J=17.5, 7 Hz, H-7α), 2.23 (1H, heptet, J=7 Hz, H-25), 2.10 (1H, m, H-23), 2.06 (1H, m, H-16), 2.05 (3H, s, $H_3$-32), 1.97 (H, dt, J=10.5, 7.5 Hz, H-17), 1.89 (1H, m, H-23), 1.77 (1H, brdd, J=13.5, 7.5 Hz, H-6β), 1.69 (1H, m, H-6α), 1.65 (1H, m, H-20), 1.57 (1H, m, H-22), 1.31 (3H, s, $H_3$-19), 1.27 (1H, t, J=12 Hz, H-1α), 1.27 (1H, dd, J=12.5, 3.0 Hz, H-5), 1.15 (1H, m, H-22), 1.08 (3H, s, $H_3$-18), 1.06 (3H, s, $H_3$-30), 1.03, 1.01 (6H, d, J=7 Hz, $H_3$-26, $H_3$-27), 0.89 (3H, s, $H_3$-29), 0.88 (3H, d, J=7 Hz, $H_3$-21); 13C NMR (CDCl$_3$) δ: 171.19 (C-31), 156.58 (C-24), 146.73 (C-14), 138.03 (C-9), 125.77 (C-8), 121.45 (C-15), 106.09 (C-28), 83.40 (C-3), 79.23 (C-12), 69.13 (C-2), 68.88 (C-11), 50.11 (C-5), 49.10 (C-17), 46.58 (C-13), 42.76 (C-1), 39.31 (C-4), 38.37 (C-10), 35.30 (C-16), 34.45 (C-22), 33.79 (C-25), 33.25 (C-20), 30.90 (C-23), 28.66 (C-30), 26.77 (C-7), 23.24 (C-19), 21.98, 21.85 (C-26, C-27), 21.28 (C-32), 18.19 (C-21), 18.00 (C-6), 16.74 (C-18), 16.69 (C-29); ESIMS (m/z): 1046 [2M+NH$_4$]$^+$, 532 [M+NH$_4$]$^+$, 497 [M+H]$^+$, 437 [M+H—H$_2$O—AcOH]$^+$, 1141[2M+CF$_3$CO$_2$]$^−$, 627 [M+CF$_3$CO$_2$]$^−$, HRE- IMS: m/z 454.3448 ([M−AcOH]$^+$, calcd for $C_{30}H_{46}O_3$: 454.3447), 439.3219 ([M−AcOH−CH$_3$]$^+$, calcd for $C_{29}H_{43}O_3$:439.3212), 311.1990 ([M−AcOH−H$_2$O−C-17 side chain]$^+$, calcd for $C_{21}H_{27}O_2$: 311.2010).

EXAMPLE 5

Isolation of Compounds A and B

A 9 L fermentation broth (pH=7.0) grown for 19 days on liquid production media was filtered through CELITE™ diatomaceous earth. The filtrate contained small amounts of Compounds A and B and was discarded. The mycelia was extracted twice each with 4 L methanol followed by 8 L of acetone. The combined acetone extract was concentrated almost to dryness and then combined with the methanol extract. The combined extracts were diluted with 8 L of water and charged over a 2 L SP207 column at a flow rate of 100 mL/min. The column was thoroughly washed with 50% aqueous methanol until the eluent became almost colorless. Elution with 70% aqueous methanol (16 L) gave fraction A which contained almost exclusively Compound A. Subsequent elution with 100% methanol (6 L) and acetone (4 L) gave fraction B that possessed a mixture of Compounds B and A. The fraction B also contained minor amounts of related congeners. An aliquot (2.8 g) of fraction B was dissolved in 8 mL methanol and 1 mL each was chromatographed, in eight equal runs, on a reverse phase HPLC (ZORBAX RX C-8, 22×250 mm, a 40 min gradient of 30 to 70% aqueous CH$_3$CN at a flow rate of 8 mL/min). Lyophilization of fractions between 24–28 min gave Compound A and lyopholization of fractions between 65–77 gave Compound B (0.26 g) both as colorless powders. Numerous fractions eluted between 4–24 min, 28–65 min and after 77 min contain a number of related minor compounds. The structure and biological activity of these compounds is under active investigation.

EXAMPLE 6

Preparation of Methoxymethyl Ethers C, D, and E

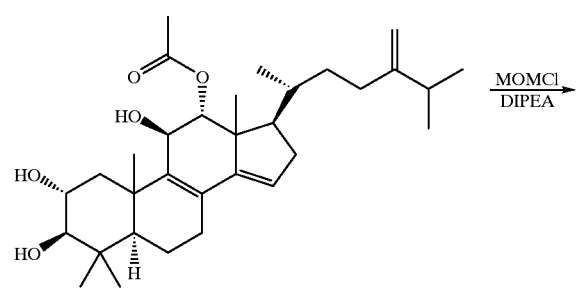

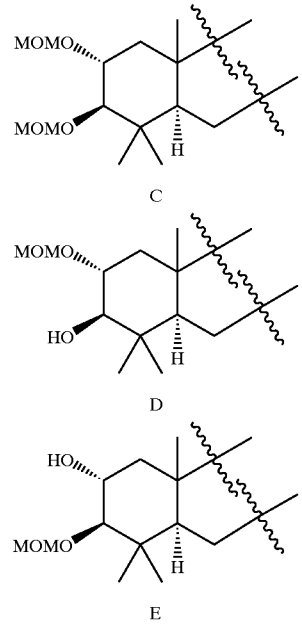

To a cold (0° C.) solution of Compound B (10 mg, 0.019 mmol) in 1 mL CH$_2$Cl$_2$ was added diisopropylethylamine (DIEA, 15.5 μL, 0.114 mmol) and methoxymethyl chloride (MOMCl, 7.4 μL, 0.095 mmol). The solution was stirred at 0° C. for 2 h followed by stirring at room temperature overnight. The reaction mixture was quenched with ice and 50 mL EtOAc was added. The organic layer was washed sequentially with 50 mL each of water, 10% aqueous citric acid, water, 10% aqueous NaHCO$_3$ followed by water and dried (Na$_2$SO$_4$). The solvent was removed under reduced pressure and products were purified by preparative TLC (SiO$_2$) using hexane-EtOAc (1:1). The three bands were eluted with EtOAc to give bis-MOMether Compound C, 2-MOMether Compound D and 3-MOMether Compound E as amorphous powder. Compound C: $^1$H NMR (CDCl$_3$) (only distinct signals are presented) δ: 5.65 (1H, brs, H-15), 5.01 (1H, d, J=2.0 Hz, H-12), 4.95 (1H, d, J=6.4 Hz, OCH$_2$O), 4.77 (2H, brs, OCH$_2$O), 4.76 (1H, d, J=6.4 Hz, OCH$_2$O), 4.75 (1H, brs, H-28),4.69 (1H, d, J=1.0 Hz, H-28),4.26 (1H, bd, J$_{H,OH=5.6}$ Hz, H-11), 3.86 (1H, ddd, J=12, 10, 4 Hz, H-2), 3.46 (3H, s, OCH$_3$), 3.43 (3H, s, OCH$_3$), 3.06 (1H, d, J=10 Hz, H-3), 2.07 (3H, s, H$_3$-32), 1.77 (1H, d, JH,OH=5.6 Hz, 11-OH), 1.32 (3H, s, H$_3$-19), 1.10 (3H, s, H$_3$-18), 1.08 (3H, s, H$_3$-30), 1.05, 1.04 (6H, d, J=6.8 Hz, H$_3$-26, H$_3$-27), 0.94 (3H, s, H$_3$-29), 0.92 (3H, d, J=6.4 Hz, H$_3$-21); ESIMS (m/z): 620 (100%, M+NH$_4$)$^+$, 603 (5%, M+H)$^+$, 585 (30%, M−H$_2$O+H)$^+$. Compound D: $^1$H NMR (CDCl$_3$) (only distinct signals are presented) δ: 5.65 (1H, t, J=2.0 Hz, H-15),5.01 (1H, d, J=1.2 Hz, H-12),4.83 (1H, d, J=6.8 Hz, OCH$_2$O),4.76 (1H, d, J=6.8 Hz, OCH$_2$O), 4.75 (1H, brs, H-28),4.69 (1H, d, J=1.2 Hz, H-28),4.27 (1H, bd, J$_{H,OH=5.2}$ Hz, H-11), 3.68 (1H, ddd, J=13.6, 9.6, 4 Hz, H-2), 3.47 (3H, s, OCH$_3$), 3.31 (1H, d, J$_{H,OH=2}$ Hz, 3-OH), 3.12 (1H, dd, J$_{2,3}$=10 Hz, J$_{H,OH=2}$ Hz, H-3), 2.07 (3H, s, H$_3$-32), 1.80 (1H, d, J$_{H,OH=6.0}$ Hz, 11-OH), 1.31 (3H, s, 1H$_3$-19), 1.12 (3H, s, H$_3$-18), 1.10 (3H, s, H$_3$-30), 1.05, 1.04 (6H, d, J=6.8 Hz, H$_3$-26, H$_3$-27), 0.93 (3H, s, H$_3$-29), 0.91 (3H, d, J=6.4 Hz, H$_3$-21); ESIMS (m/z): 576 (100%, M+NH$_4$)$^+$, 541 (40%, M–H$_2$O+H)$^+$. Compound E: $^1$H NMR (CDCl$_3$) (only distinct signals are presented) δ: 5.64 (1H, t, J=2.0 Hz, H-15), 5.02 (1H, d, J=1.2 Hz, H-12), 4.87 (1H, d, J=6.4 Hz, OCH$_2$O), 4.75 (1H, brs, H-28), 4.69 (1H,brs, H-28), 4.66 (1H, d, J=6.4 Hz, OCH$_2$O), 4.31 (1H, bd, J$_{H,OH=4.4}$ Hz, H-11), 3.84 (1H, ddd, J=12.8, 9.6, 4 Hz, H-2), 3.49 (3H, s, OCH$_3$), 2.85 (1H, dd, J$_{2,3}$=9.6 Hz, J$_{H,OH=2}$ Hz, H-3), 2.05 (3H, s, H$_3$-32), 1.95 (1H, d, J$_{H,OH=5.2}$ Hz, 11-OH), 1.33 (3H, s, H$_3$-19), 1.10 (3H, s, H$_3$-18), 1.05, 1.04 (6H, d, J=6.8 Hz, H$_3$-26, H$_3$-27), 1.02 (3H, s, H$_3$-30), 0.93 (3H, s, H$_3$-29), 0.92 (3H, d, J=6.4 Hz, H$_3$-21); ESIMS (m/z): 576 (60%, M+NH$_4$)$^+$, 541 (90%, M–H$_2$O+H)$^+$, 481 (100%, M+H—H$_2$O—AcOH)$^+$.

EXAMPLE 7
Preparation of Methoxymethyl Ethers F, G, and H

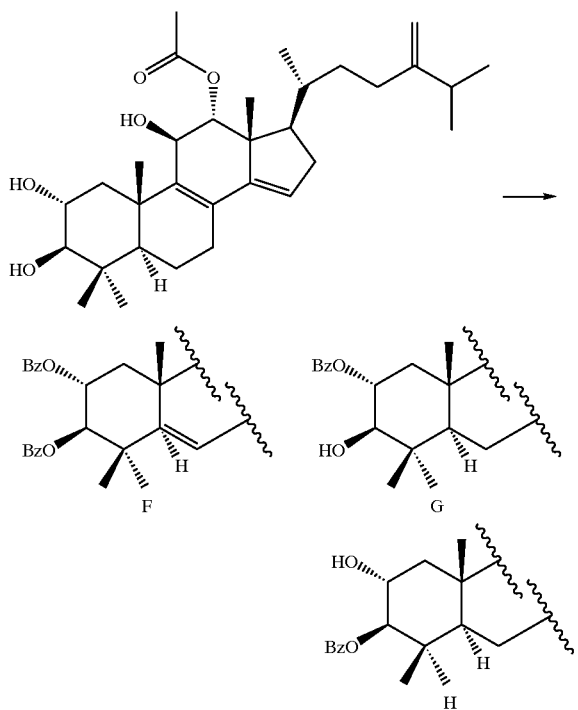

Triethylamine (20 μL), DMAP (5 mg) and benzoic anhydride (17.2 mg, 0.076 mmol) was added to a stirred solution of Compound B (10 mg, 0.019 mmol) in anhydrous THF (1 mL). The reaction mixture was stirred overnight under nitrogen. Ice (5 g) was added to quench the reaction and the mixture was diluted with EtOAc (50 mL). The organic layer was separated and sequentially washed with 20 mL each of water, 10% aqueous citric acid, water, 10% aqueous NaHCO$_3$ followed by water, dried (Na$_2$SO$_4$), and EtOAc was evaporated under reduced pressure. The mixture was chromatographed by preparative TLC (SiO$_2$, hexane-EtOAc, 7:3) to give Compounds F, G, and H all as colorless amorphous powders. Compound F: $^1$H NMR (CDCl$_3$) (only distinct signals are presented) δ: 7.99 (2H, dd, J=7.6, 1.6 Hz, ArH), 7.92 (2H, dd, J=8.4, 1.2 Hz, ArH), 7.47 (2H, m, ArH), 7.37 (2H, t, J=8 Hz, ArH), 7.35 (2H, t, J=7.6 Hz, ArH), 5.68 (1H, brs, H-15), 5.62 (1H, dt, J=11.6, 4.4 Hz, H-2), 5.26 (1H, d, J=10.4 Hz, H-3), 4.99 (11H, d, J=2.0 Hz, H-12), 4.75 (1H, brs, H-28), 4.69 (1H, d, J=1.0 Hz, H-28), 4.23 (1H, bd, J$_{H,OH}$=5.0 Hz, H-11), 2.10 (3H, s, H$_3$-32), 1.83 (1H, d, JH,OH=5.6 Hz, 11-OH), 1.52 (3H, s, CH$_3$), 1.20 (3H, s, CH$_3$), 1.11 (3H, s, CH$_3$), 1.06 (3H, s, CH$_3$), 1.06, 1.05 (6H, d, J=6.8 Hz, H$_3$-26, H$_3$-27), 0.92 (3H, d, J=6.4 Hz, H$_3$-21); ESIMS (m/z): 1462 (85%, 2M+NH$_4$)$^+$, 740 (100%, M+NH$_4$)$^+$, 705 (35%, M–H$_2$O+H)$^+$. Compound G: $^1$H NMR (CDCl$_3$) (only distinct signals are presented) δ: 8.10 (2H, dd, J=7.6, 1.6 Hz, ArH), 7.60 (1H, t, J=7.6 Hz, ArH), 7.48 (2H, t, J=8 Hz, ArH), 7.35 (2H, t, J=7.6 Hz, ArH), 5.67 (1H, brs, H-15), 5.36 (1H, dt, J=11.2, 4.4 Hz, H-2), 4.99 (1H, brs, H-12), 4.75 (1H, brs, H-28), 4.69 (1H, d, J=1.0 Hz, H-28), 4.23 (1H, brs, H-11), 3.41 (1H, d, J=10 Hz, H-3), 2.09 (3H, s, H$_3$-32), 1.43 (3H, s, CH$_3$), 1.14 (3H, s, CH$_3$), 1.10 (3H, s, CH$_3$), 1.05, 1.04 (6H, d, J=6.8 Hz, H$_3$-26, H$_3$-27), 1.02 (3H, s, CH$_3$), 0.91 (3H, d, J=6.4 Hz, H$_3$-21); ESIMS (m/z): 1254 (10%, 2M+NH$_4$)$^+$, 636 (100%, M+NH$_4$)$^+$, 601 (30%, M–H$_2$O+H)$^+$. Compound H: $^1$H NMR (CDCl$_3$) (only distinct signals are presented) δ: 8.12 (2H, d, J=7.2, ArH), 7.61 (1H, t, J=7.6 Hz, ArH), 7.49 (2H, t, J=8 Hz, ArH), 7.35 (2H, t, J=7.6 Hz, ArH), 5.67 (1H, brs, H-15), 5.02 (1H, brs, H-12),4.84 (1H, d, J=10 Hz, H-3),4.76 (1H, brs, H-28),4.70 (1H, d, J=1.0 Hz, H-28),4.32 (1H, brs, H-1 1), 4.11 (1H, dt, J=10,3.6 Hz, H-2), 2.10 (3H, s, H$_3$-32), 1.39 (3H, s, CH$_3$), 1.12 (3H, s, CH$_3$), 1.11 (3H, s, CH$_3$), 1.06, 1.05 (6H, d, J=6.8 Hz, H$_3$-26, H$_3$-27), 1.01 (3H, s, CH$_3$), 0.92 (3H, d, J=6.4 Hz, H$_3$-21); ESIMS (m/z): 1254 (10%, 2M+NH$_4$)$^+$, 636 (100%, M+NH$_4$)$^+$, 601 (30%, M–H$_2$O+H)$^+$.

EXAMPLE 8
Preparation of Hemisuccinates J and K

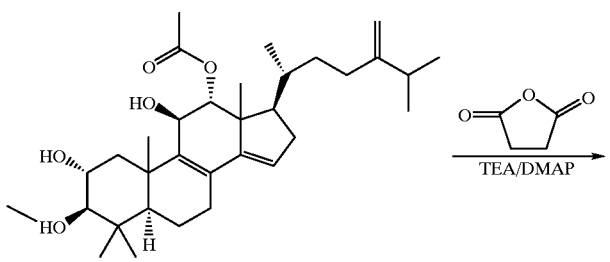

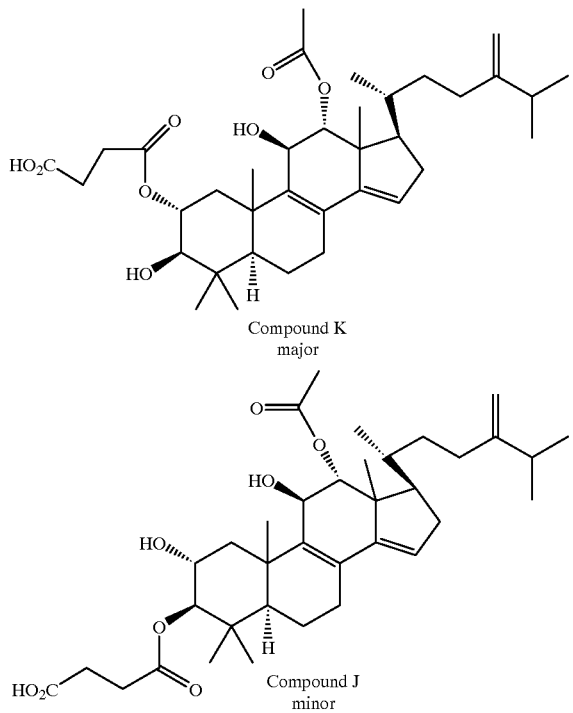

Compound K
major

Compound J
minor

To a THF (2 mL) solution of Compound B (10 mg, 0.019 mmol) was added triethylamine (60 μL), DMAP (5 mg) and succinic anhydride (22 mg). The mixture was stirred at room temperature overnight and heated at 50° C. for 2 h. The reaction mixture was allowed to cool down and then ice followed by addition of EtOAc (50 mL). The layers were separated and the organic layer was sequentially washed with 2×20 mL each of water, 10% aqueous citric acid, water, and dried ($Na_2SO_4$). EtOAc was removed under reduced pressure. Chromatography of the mixture on reverse phase HPLC (ZORBAX RX C-8, 22×250 mm, gradient of 60% to 75% $CH_3CN$ in $H_2O$, both containing 0.05% TFA, flow rate 8 mL/min) followed by lyophilization gave Compound J and Compound K as colorless amorphous powders. Compound J: $^1H$ NMR ($CDCl_3$) (only distinct signals are presented) δ: 5.64 (1H, brs, H-15), 5.04 (1H, brs, H-12), 4.75 (1H, brs, H-28), 4.69 (1H, d, J=1.0 Hz, H-28), 4.65 (1H, d, J=9.6 Hz, H-3), 4.23 (1H, brs, H-11), 4.00 (1H, m, H-2), 2.73 (4H, m, 2×$CH_2CO$), 2.07 (3H, s, $H_3$-32), 1.34 (3H, s, $CH_3$), 1.11 (3H, s, $CH_3$), 1.05, 1.04 (6H, d, J=6.8 Hz, $H_3$-26, $H_3$-27), 0.97 (3H, s, $CH_3$), 0.93 (3H, s, $CH_3$), 0.91 (3H, d, J=6.4 Hz, $H_3$-21); ESIMS (m/z): 1246 (10%, 2M+$NH_4$)$^+$, 632 (100%, M+$NH_4$)$^+$, 597 (35%, M−$H_2O$+H)$^+$. Compound K: $^1H$ NMR ($CDCl_3$) (only distinct signals are presented) δ: 5.65 (1H, brs, H-15), 5.15 (1H, dt, J=11.6, 4.4 Hz, H-2), 4.98 (1H, brs, H-12), 4.76 (1H, brs, H-28), 4.69 (1H, d, J=1.0 Hz, H-28), 4.22 (1H, brs, H-11), 3.29 (1H, d, J=10 Hz, H-3), 2.76 (2H, m, 2×$CH_2CO$), 2.68 (2H, m, 2×$CH_2CO$), 2.10 (3H, s, $H_3$-32), 1.36 (3H, s, $CH_3$), 1.10 (3H, s, $CH_3$), 1.09 (3H, s, $CH_3$), 1.05, 1.04 (6H, d, J=6.8 Hz, $H_3$-26, $H_3$-27), 0.95 (3H, s, $CH_3$), 0.91 (3H, d, J=6.4 Hz, $H_3$-21); ESIMS (m/z): 1246 (10%, 2M+$NH_4$)$^+$, 632 (100%, M+$NH_4$)$^+$, 597 (35%, M−$H_2O$+H)$^+$.

EXAMPLE 9
Preparation of Hemisuccinate Methyl Esters L and M

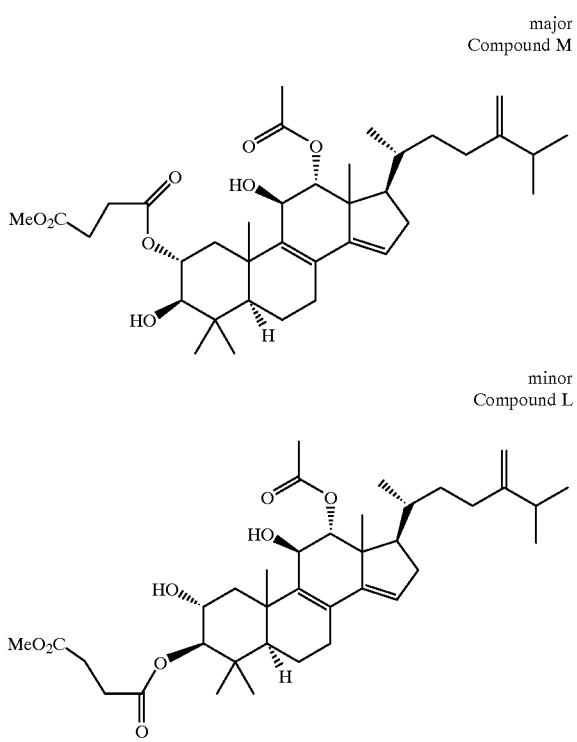

major
Compound M minor
Compound L

A mixture of 16 mg of hemisuccinates (Compounds J and K), described in the Example 7, was dissolved in 0.1 mL $CH_2Cl_2$ and cooled to 0° C. An ethereal solution of freshly prepared diazomethane was added and the solution was kept at 0° C. overnight. Volatile material was evaporated under a stream of nitrogen and the methyl esters were purified by preparative TLC (SiO$_2$, hexane-EtOAc, 3:1). Elution of the bands with EtOAc gave mono methyl esters Compounds M and L as amorphous powders. Compound M: $^1$H NMR (CDCl$_3$) (only distinct signals are presented) δ: 5.63 (1H, t, J=2.8 Hz, H-15), 5.15 (1H, ddd, 11.6, 10, 4.4 Hz, H-2), 4.97 (1H, d, J=1.6 Hz, H-12), 4.73 (1H, brs, H-28), 4.67 (1H, d, J=1.0 Hz, H-28), 4.18 (1H, brs, H-11), 3.70 (3H, s, OCH$_3$), 3.23 (1H, d, 10 Hz, H-3), 2.68 (4H, m, 2×CH$_2$CO), 2.07 (3H, s, H$_3$-32), 1.34 (3H, s, CH$_3$), 1.09 (3H, s, CH$_3$), 1.07 (3H, s, CH$_3$), 1.03, 1.02 (6H, d, J=6.8 Hz, H$_3$-26, H$_3$-27), 0.94 (3H, s, CH$_3$), 0.89 (3H, d, J=6.4 Hz, H$_3$-21); ESIMS (m/z): 629 (100%, M+H)$^+$, HREIMS (m/z): 628.3978 (calcd for C$_{37}$H$_{56}$O$_8$: 428.3975). Compound L: $^1$H NMR (CDCl$_3$) (only distinct signals are presented) δ: 5.63(1H, t, J=2.8 Hz, H-15), 4.98 (1H, d, J=1.6 Hz, H-12), 4.73 (1H, brs, H-28), 4.67 (1H, d, J=1.6 Hz, H-28), 4.62 (1H, d, J=9.6 Hz, H-3), 4.27 (1H, brs, H-1 1), 3.95 (1H, ddd, J=11.6, 10,4.4 Hz, H-2), 3.70 (3H, s, OCH$_3$), 2.68 (4H, m, 2×CH$_2$CO), 2.05 (3H, s, H$_3$-32), 1.32 (3H, s, CH$_3$), 1.08 (3H, s, CH$_3$), 1.03, 1.02 (6H, d, J=6.8 Hz, H$_3$-26, H$_3$-27), 0.94 (3H, s, CH$_3$), 0.92 (3H, s, CH$_3$), 0.89 (3H, d, J=6.4 Hz, H$_3$-21); ESIMS (m/z): 629 (50%, M+H)$^+$, HREIMS (m/z): 628.4009 (calcd for C$_{37}$H$_{56}$O$_8$: 428.3975).

EXAMPLE 10
Preparation of Succinic Acid Hydroxymate N

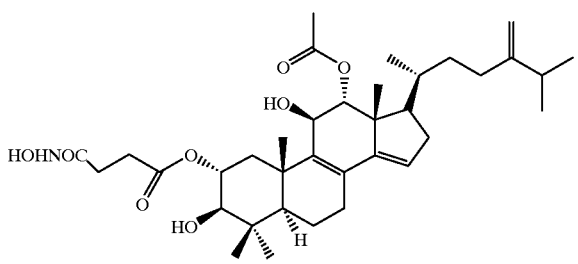

Compound N

To a cooled (−40° C.) solution of Compound K (10 mg, 0.016 mmol, Example 7) in THF (0.5 mL) was added N-methylmorpholine (15 μL) followed by allyl chloroformate (10 μL). The reaction mixture was allowed to warm to room temperature. After stirring for 30 min under nitrogen it was re-cooled at −23° C. and an aqueous solution of hydroxylamine was added via a syringe. The mixture was stirred at 0° C. for 30 min and then quenched with ice and diluted with EtOAc (50 mL). The ethyl acetate layer was sequentially washed with 20 mL each of 10% aqueous citric acid, water, 10% aqueous NaHCO$_3$ and water. EtOAc extract was dried (Na$_2$SO$_4$), concentrated under reduced pressure and chomatographed by reverse phase HPLC (ZORBAX RX C-8, 22×250 mm, 20 to 80% CH$_3$CN in H$_2$O (+0.1% TFA) gradient in 40 min, at 8 mL/min). The fractions containing the product were lyophilized to give hydroxymate Compound N (4 mg) as an amorphous powder. $^1$H NMR (CDCl$_3$) δ: (only distinct signals are listed, spectrum was very broad) 5.64 (1H, brs, H-15), 5.14 (1H, m, H-2), 4.98 (1H, brs, H-12), 4.75 (1H, brs, H-28), 4.69 (1H, brs, H-28), 4.19 (1H,brs, H-11), 3.30 (4H, m, 2×CH$_2$), 2.75 (1H, H-3), 2.23 (1H, heptet, J=7.2 Hz, H-25), 2.09 (3H, s, COCH$_3$), 1.35 (3H, s, CH$_3$), 1.09 (6H, s, 2×CH$_3$), 1.05, 1.04 (6H, d, J=6.8 Hz, H$_3$-26, H$_3$-27),0.94 (3H, s, CH$_3$),0.90 (3H, d, J=6 Hz, H$_3$-21), ESIMS m/z: 630 (M+H)$^+$.

EXAMPLE 11
Preparation of Compound O

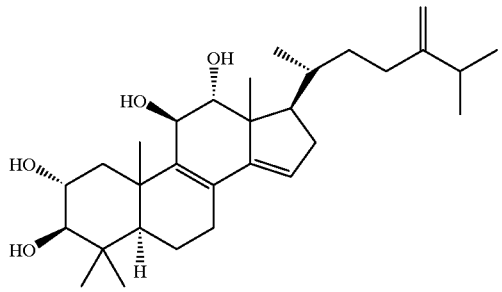

Compound O

To a solution of Compound B (10 mg) in dioxane-water (2:1, 1.5 mL) was added LiOH (13.4 mg) and the yellowish solution was stirred at room temperature overnight. EtOAc (50 mL) was added and the solution was washed with 2× 20 mL of water. The EtOAc layer was dried (Na$_2$SO$_4$), evaporated under reduced pressure and chromatographed on preparative TLC (SiO$_2$, hexane-EtOAc, 3:7). Elution of the major band gave Compound O as colorless amorphous powder. $^1$H NMR (CDCl$_3$+CD$_3$OD, 10:1) δ: 5.59 (1H, brs, H-15), 4.66 (1H, brs, H-28), 4.60 (1H, brs, H-28), 4.23 (1H, brs, H-11), 3.69(11H, dt, J=11.2,4 Hz, H-2), 3.69(11H, d, J=1.6 Hz, H-12), 2.90 (1H, d, J=9.2 Hz, H-3), 2.36 (2H, m, H-16, H-7α), 2.27 (1H, dd, J=11,6 Hz, H-1β), 2.20 (1H, m, H-7α), 2.20(1H, m, H-17),2.19 (1H, m, H-25), 2.07 (1H, m, H-23), 1.97 (1H, m, H-16), 1.86 (1H, m, H-23), 1.69 (1H, m , H-6β), 1.61 (1H, m, H-6α), 1.61 (11H, m, H-20), 1.51 (1H, m, H-22), 1.27 (11H, t, J=12 Hz, H-1α), 1.23 (3H, s, H$_3$-19), 1.20 (2H, m, H-5, H-22), 0.97 (3H, s, H$_3$-18), 0.97 (3H, d, J=6.4 Hz, H$_3$-21), 0.96 (3H, s, H$_3$-30), 0.96,0.95 (6H, d, J=5.6 Hz, H$_3$-26, H$_3$-27), 0.81 (3H, s, H$_3$-29), HREIMS (m/z): 472.3543 (M$^+$, calcd for C$_{30}$H$_{48}$O$_4$: 472.3552).

EXAMPLE 12
Preparation of Triacetate Compound P

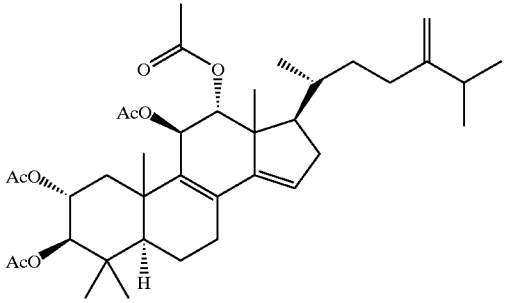

Compound P

To a solution of Compound B (10 mg) in pyridine (0.5 mL) was added acetic anhydride (0.3 mL) and the solution was stirred at room temperature overnight under an inert atmosphere followed by heating at 50° C. for 3 h. Methanol was added to consume excess acetic anhydride. The solvent and volatile material was removed under a stream of N$_2$. The product was purified by preparative TLC (SiO$_2$, hexane-EtOAc, 7:3). The band was eluted with EtOAc. Evaporation of EtOAc under reduced pressure afforded the triacetate Compound P as a colorless foam. $^1$H NMR (CDCl$_3$) δ: 5.73

(1H, brs, H-15), 5.33 (1H, brs, H-11), 5.18 (1H, brdt, J=11.6, 4.4 Hz, H-2), 5.13 (1H, d, J=2.0 Hz, H-12),4.77 1H, d, J=10 Hz, H-3), 4.74 (1H, brs, H-28), 4.68 (1H, brs, H-28), 2.50 (1H, m, H-16), 2.48 (1H, m, H-7,), 2.40 (1H, brdd, J=18.4, 6.8 Hz, H-7α), 2.24 (1H, doublet of heptet, J=6.4, 0.8 Hz, H-25), 2.13 (2H, m, H-23, H-16), 2.10 (3H, s, COCH$_3$), 2.09 (3H, s, COCH$_3$), 2.08 (3H, s, COCH$_3$), 2.03 (3H, s, COCH$_3$), 1.95 (1H, dd, J=12, 4 Hz, H-1), 1.86 (1H, m, H-23), 1.85 (1H, m, H-23), 1.82 (1H, m, H-5), 1.81 (1H, m, H-6), 1.70 (1H, m, H-6), 1.61 (1H, m, H-20), 1.56 (1H, m, H-22), 1.41 (1H, t, J=12 Hz, H-1α), 1.38 (1H, m, H-5), 1.27 (3H, s, H$_3$-19), 1.16 (2H, m, H-22), 1.05 (3H, s, CH$_3$), 1.04, 1.03 (6H, d, J=6.8 Hz, H$_3$-26, H$_3$-27), 0.99 (3H, s, CH$_3$), 0.95 (3H, s, CH$_3$), 0.89 (3H, d, J=6.4 Hz, H$_3$-21), ESIMS (m/z): 658 (M+NH$_4$)$^+$, HREIMS (m/z): 598.3837 (M–COCH$_2$, calcd for C$_{36}$H$_{54}$O$_7$: 598.3869).

EXAMPLE 13
Preparation of 2,3-Acetonide Compound Q

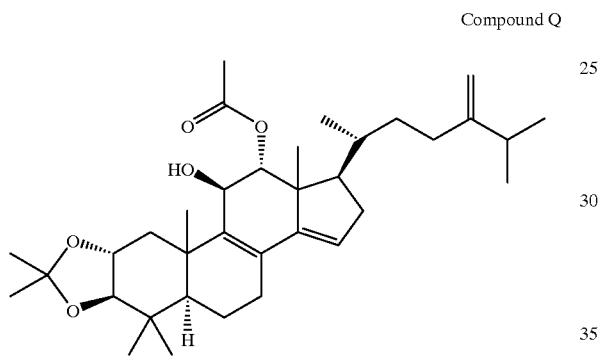

Compound Q

To a solution of Compound B (10 mg) in CH$_2$Cl$_2$ (1 mL) was added 2,2-dimethoxy propane (0.1 mL) and pyridinium p-toluenesulfonic acid (5 mg) and the solution was stirred at room temperature for 30 min. Water (20 mL) and EtOAc (50 mL) was added and the layers were separated. The organic layer was sequentially washed with 20 mL each of 10% aqueous citric acid, water, 10% aqueous NaHCO$_3$ and water. EtOAc extract was dried (Na$_2$SO$_4$), concentrated under reduced pressure and chomatographed over a preparative TLC (SiO$_2$, hexane-EtOAc, 7:3). Elution of the band with EtOAc and evaporation of the solvent gave acetonide Compound Q as an amorphous powder. $^1$H NMR (CDCl$_3$) δ: 5.65 (1H, brs, H-15), 5.01 (1H, d, J=2.0 Hz, H-12), 4.75 (1H, brs, H-28), 4.69 (1H, d, J=1.6 Hz, H-28),4.28 (1H,brd, J$_{H,OH}$ =4.8 HZ, H-11), 3.85 (1H, ddd, J=12.8, 9.6, 3.6 Hz, H-2), 3.11 (1H, d, J=9.6 Hz, H-3), 2.54 (1H, dd, J=10.8, 3.2 Hz, H-1), 2.49 (1H, m, H-7), 2.47 (1H, m, H-16), 2.37 (1H, brdd, J=18, 7.2 Hz, H-7α), 2.25 (1H, heptet, J=6.8 Hz, H-25), 2.09 (1H, m, H-16), 2.08 (3H, s, COCH$_3$), 2.06 (1H, m, H-23), 1.95 (1H, m, H-17), 1.92 (1H, m, H-23), 1.91 (1H, d, J=5.2 Hz, OH), 1.83 (1H, m, H-6), 1.71 (1H, m, H-6), 1.65 (1H, m, H-20), 1.57 (1H, m, H-22), 1.47, 1.45 (3H each, s, 2×CH$_3$), 1.45 (1H, t, J=13.2 Hz, H-1α), 1.36 (3H, s, CH$_3$), 1.29 (1H, dd,J=12.8,2.4 Hz, H-5), 1.20 (1H, m, H-22), 1.10 (6H, s, 2×CH$_3$), 1.05, 1.04 (6H, d, J=6.8 Hz, H$_3$-26, H$_3$-27), 0.98 (3H, s, CH$_3$), 0.91 (3H, d, J=6.4 Hz, H$_3$-21), HREIMS (m/z): 554.3947 (M$^+$, calcd for C$_{35}$H$_{54}$O$_5$: 554.3971).

EXAMPLE 14
Preparation of 2,3-Epoxide Compound S via Mesolate Compound R

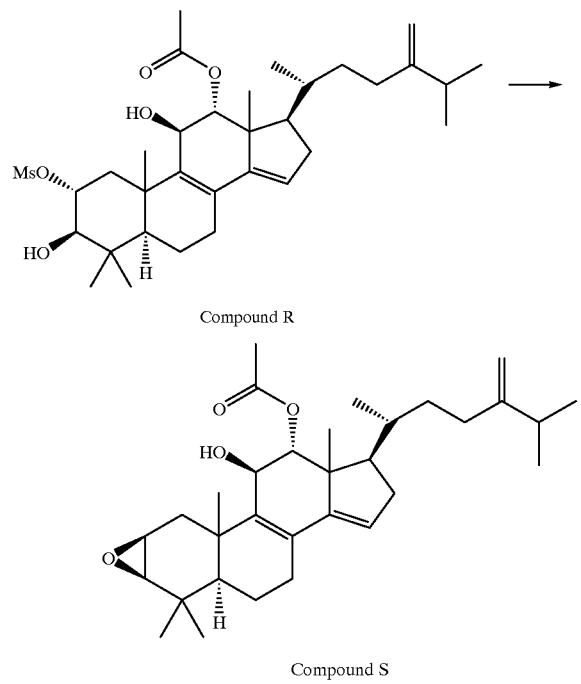

Compound R

Compound S

To a cooled (–40° C.) solution of Compound B (42 mg, 0.08 mmol) in CH$_2$Cl$_2$ (1 mL) was added diisopropylethylamine (33 μL), dimethylaminopyridine (5 mg) and methane sulfonyl chloride (14 μL). The reaction mixture was stirred for 20 min and was allowed to warm to room temperature and quenched by addition of ice. EtOAc (50 mL) was added and the layers were separated. The organic layer was sequentially washed with 20 mL each of water, 10% aqueous citric acid, water, 10% aqueous NaHCO$_3$ and finally with water, dried (Na$_2$SO$_4$), evaporated under reduced pressure to give clean 2-mesolate Compound R as a foam. $^1$H NMR (CDCl$_3$) δ: only distinct signals are listed. 5.64 (1H, brs, H-15), 5.00 (1H, d, J=0.8 Hz, H-12), 4.81 (1H, ddd, J=11.6, 9.6, 4.0 Hz, H-2), 4.75 (11H, brs, H-28), 4.68 (11H, d, J=0.2 Hz, H-28), 4.19(1H, brs, H-11), 3.27(1H, d, J=9.6 Hz, H-3), 3.16 (3H, brs, SOCH$_3$), 2.11 (3H, s, COCH$_3$), 1.30 (3H, s, CH$_3$), 1.11 (3H, s, CH$_3$), 1.09 (3H, s, CH$_3$), 1.05, 1.04 (6H, d, J=6.8 Hz, H$_3$-26, H$_3$-27), 0.96 (3H, s, CH$_3$), 0.90 (3H, d, J=6.4 Hz, H$_3$-21), ESIMS (m/z): 610 (M+NH$_4$)$^+$. The mesolate Compound R (12 mg) in 1 mL of toluene and 50 μL of DBU was heated at 50° C. for 30 min. Ice followed by EtOAc (50 mL) was added to the reaction after it was cooled to room temperature. The EtOAc layer was sequentially washed with 20 mL each of water, 10% aqueous citric acid, water, 10% aqueous NaHCO$_3$ and finally with water, dried (Na$_2$SO$_4$), evaporated under reduced pressure and chromatographed over a preparative TLC (SiO$_2$, hexane-EtOAc, 7:3). The band was eluted with EtOAc to give 2,3-epoxide Compound S as an amorphous powder. $^1$H NMR (CDCl$_3$) δ: 5.62 (1H, t, J=2 Hz, H-15), 5.01 (1H, d, J=2.4 Hz, H-12), 4.73 (1H, brs, H-28), 4.67 (1H, d, J=2 Hz, H-28), 4.31 (1H, brd, J$_{H,OH}$=6.4 HZ, H-11), 3.34(11H, dt, J=4,2 Hz, H-2), 2.86 (1H, d, J=4.4 Hz, H-3), 2.51 (1H, dd, J=14.4, 2 Hz, H-1), 2.45 (11H, ddd, J=16, 6.8, 3.2 Hz, H$_1$-16), 2.32 (2H, m, H-7), 2.23 (11H, heptet, J=7.2 Hz, H-25), 2.10 (11H, m, 1H-16), 2.07 (1H, m, H-23), 2.06 (3H, s, COCH$_3$), 1.99 (1H, m, H-17), 1.89 (1H, m, H-23), 1.79 (11H, d, J=5.6 Hz, OH), 1.65 (1H, m, H-20), 1.61 (2H, m, H-6), 1.60, 1.54 (2H, m, H-22), 1.48 (1H, d, J=14 Hz, H-1α), 1.39 (3H, s, CH$_3$), 1.16 (1H, m, H-22), 1.084 (6H, s, 2×CH$_3$), 1.078 (3H, s, CH$_3$), 1.03, 1.02 (6H, d, J=6.8 Hz, H$_3$-26, H$_3$-27), 0.89 (3H, d, J=6.4 Hz, H$_3$-21), ESIMS m/z: 514 (M+NH$_4$)$^+$, HREIMS (m/z): 436.3344 ([M−AcOH]$^+$, calcd for C$_{30}$H$_{44}$O$_2$: 436.3341).

EXAMPLE 15
Preparation of t-Boc-glycine Esters Compounds T and U

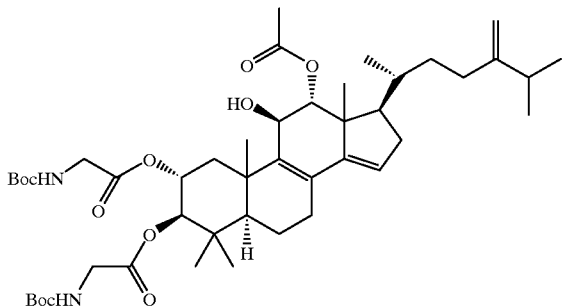

Compound T

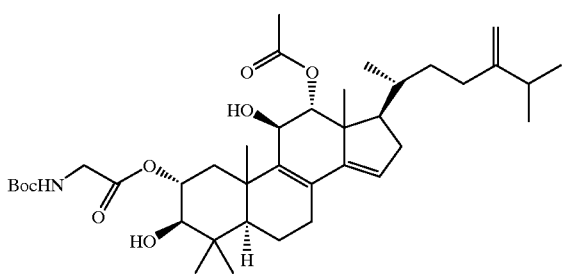

Compound U

To an anhydrous solution of Compound B (40 mg, 0.078 mmol) in a 2:1 mixture of CH$_2$Cl$_2$-THF (1.5 mL) was added N-t-Boc-glycine-succinimide ester (103 mg, 0.39 mmol) followed by diisopropylethylamine (64 μL) and dimethylaminopyridine (5 mg). The homogeneous mixture was stirred for overnight under nitrogen followed by heating at 50° C. for 2 h. The reaction mixture was quenched by addition of ice and was diluted with EtOAc (50 mL). The organic layer was sequentially washed with 20 mL each of water, 10% aqueous citric acid, water, 10% aqueous NaHCO$_3$ and finally with water, dried (Na$_2$SO$_4$), evaporated under reduced pressure and chromatographed over a preparative TLC (SiO$_2$, hexane-EtOAc, 7:3). The two bands were eluted with EtOAc to give diester Compound T and monoester Compound U; both as amorphous powders. Compound T: $^1$H NMR (CDCl$_3$) δ: (only distinct signals are listed) 5.66 (1H, brs, H-15), 5.48 (1H, brt, J=6 Hz, NH), 5.37 (1H, dt, J=11.6,3.6 Hz, H-2), 5.30 (1H, t, J=6 Hz, NH), 4.99 (1H, d, J=0.8 Hz, H-12), 4.81 (1H, d, J=10 Hz, H-3), 4.75 (1H, brs, H-28), 4.69 (1H, d, J=1.2 Hz, H-28), 4.20 (1H,brd, J$_{H,OH}$=4.8 Hz, H-11), 3.93 (2H, m, gly-CH$_2$), 3.83 (2H, m, gly-CH$_2$), 2.26 (1H, heptet, J=7.2 Hz, H-25), 2.10 (3H, s, COCH$_3$), 1.94 (1H, d, J=5.2 Hz, OH), 1.48, 1.46 (9H each, s, C(CH$_3$)$_3$), 1.38 (3H, s, CH$_3$), 1.09 (3H, s, CH$_3$), 1.05, 1.04 (6H, d, J=6.8 Hz, H$_3$-26, H$_3$-27), 1.00 (3H, s, CH$_3$), 0.95 (3H, s, CH$_3$), 0.92 (3H, d, J=6.8 Hz, H$_3$-21), ESIMS m/z: 846 (M+NH$_4$)$^+$. Compound U: $^1$H NMR (CDCl$_3$) δ: (only distinct signals are listed) 5.66 (1H, brs, H-15),5.18 (1H, dt, J=11.6,4 Hz, H-2),5.10(11H, t, J=6 Hz, NH), 4.99 (1H, d, J=0.8 Hz, H-12),4.76 (1H, brs, H-28),4.69 (1H, d, J=1.6 Hz, H-28),4.19 (1H,brd, J$_{H,OH}$=5.2 Hz, H-11), 3.97 (1H, dd, J=17.6, 5.0 Hz, gly-CH), 3.92 (11H, dd, J=17.6, 5.6 Hz, gly-CH), 3.22 (1H, d, J=7.6 Hz, H-3), 2.26 (1H, heptet, J=7.2 Hz, H-25), 2.10 (3H, s, COCH$_3$), 1.93 (1H, d, J=5.2 Hz, OH), 1.48 (9H, s, C(CH$_3$)$_3$), 1.37 (3H, s, CH$_3$), 1.10 (3H, s, CH$_3$), 1.09 (3H, s, CH$_3$), 1.06, 1.05 (6H, d, J=6.8 Hz, 1H$_3$-26, H$_3$-27), 0.96 (3H, s, CH$_3$), 0.91 (3H, d, J=6.8 Hz, H$_3$-21), ESIMS m/z: 689 (M+NH$_4$)$^+$.

EXAMPLE 16
Preparation of Fmoc-Glycine Esters Compounds V and W

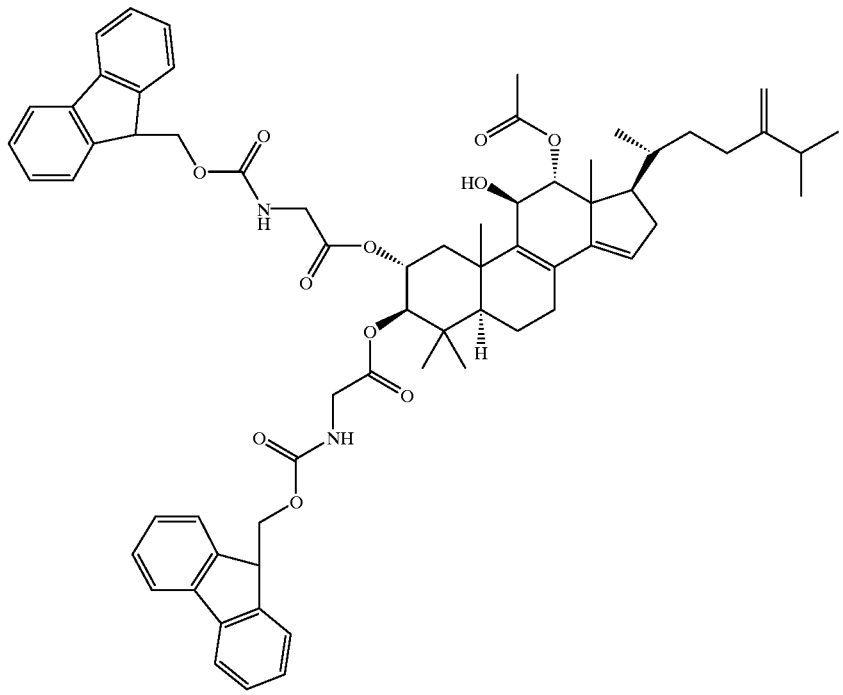

Compound V

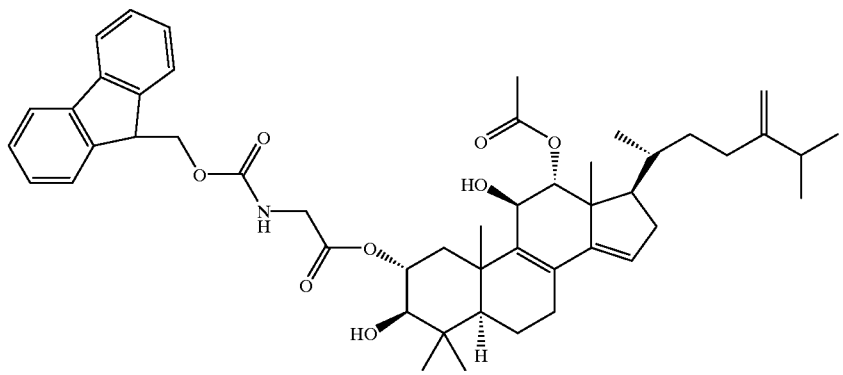

Compound W

Diisopropylethyl amine (128 μL, 0.7 mmol) and dimethylaminopyridine (10 mg) followed by Fmoc-glycine-pentafluorophenyl ester were added to a solution of Compound B (80 mg, 0.14 mmol) in a 2:3 mixture of $CH_2Cl_2$-THF (5 mL). The solution was stirred overnight under nitrogen. Water followed by EtOAc (50 mL) was added after completion of the reaction and the layers were separated. The organic layer was sequentially washed with 2×20 mL each of water, 10% aqueous citric acid, water, 10% aqueous $NaHCO_3$ and finally with water, dried ($Na_2SO_4$), evaporated under reduced pressure and chromatographed over preparative TLC ($SiO_2$, hexane-EtOAc, 7:3). The two bands were eluted with EtOAc to give diester Compound V and monoester Compound W both as amorphous pale powders. Compound V: $^1H$ NMR ($CDCl_3$) δ: (only distinct signals are listed) 7.76 (4H, d, J=7.5 Hz, ArH), 7.60 (4H, t, J=8 Hz, ArH), 7.38 (4H, t, J=7.5 Hz, ArH), 7.26 (4H, m, ArH), 5.85 (1H, t, J=6 Hz, NH), 5.72 (1H, t, J=6.5 Hz, NH), 5.67 (1H, t, J=2.5 Hz, H-15), 5.37 (1H, ddd, J=12, 10.5, 4.5 Hz, H-2), 4.99 (1H, d, J=1.5 Hz, H-12), 4.82 (1H, d, J=10.5 Hz, H-3), 4.74 (1H, brs, H-28), 4.69 (1H, d, J=1.5 Hz, H-28), 4.40–4.30 (4H,m, 2×$CH_2O$—), 4.24–4.16 (3H, m, Fmoc-CH, H-11), 3.90 (4H, m, 2×gly-$CH_2$), 2.25 (1H, doublet of heptet, J=7, 1 Hz, H-25), 2.04 (3H, s, $COCH_3$), 1.37 (3H, s, $CH_3$), 1.08 (3H, s, $CH_3$), 1.04, 1.03 (6H, d, J=6.8 Hz, $H_3$-26, $H_3$-27), 0.98 (3H, s, $CH_3$), 0.94 (3H, s, $CH_3$), 0.91 (3H, d, J=6.8 Hz, $H_3$-21), HRFABMS m/z: 1095.5364 (calcd for $C_{66}H_{76}N_2O_{11}Na$: 1095.5347). Compound W: $^1H$ NMR ($CDCl_3$) δ: (only distinct signals are listed) 7.81 (2H, d, J=7.5 Hz, ArH), 7.65 (2H,m, ArH), 7.43 (2H, brt, J=8 Hz, ArH), 7.36 (2H, m, ArH), 5.67 (1H,t,J=2.5 Hz, H-15),5.51 (1H,t,J=6.0 Hz, NH),5.14(1H, ddd, J=14, 11.5, 4.0 Hz, H-2), 5.00 (1H, d, J=1.0 Hz, H-12), 4.76 (1H, d, J=1.5 Hz, H-28), 4.70 (1H, q, J=1.5 Hz, H-28), 4.45 (2H, d, J=7.5 Hz, Fmoc-$CH_2$), 4.28 (1H, t, J=7.5 Hz, Fmoc-CH), 4.00 (2H, m, gly-$CH_2$), 3.19 (1H, d, J=10 Hz, H-3), 2.27 (1H, doublet of heptet, J=7, 1 Hz, H-25), 2.05 (3H, s, $COCH_3$), 1.37 (3H, s, $CH_3$), 1.10 (3H, s, $CH_3$), 1.06 (3H, s, $CH_3$), 1.06, 1.05 (6H, d, J=6.8 Hz, $H_3$-26, $H_3$-27), 0.94 (3H, s, $CH_3$), 0.92 (3H, d, J=6.5 Hz, $H_3$-21), HRFABMS m/z: 816.4488 (calcd for $C_{49}H_{63}NO_8Na$: 816.4452).

EXAMPLE 17

Preparation of Glycine Ester Compound X

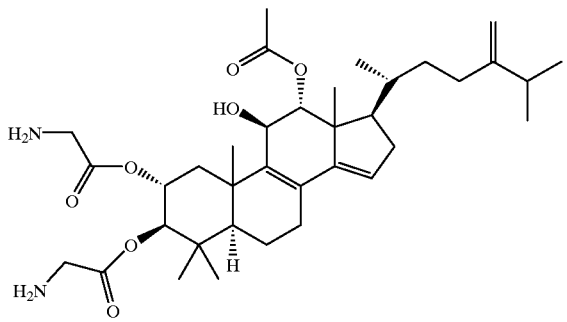

Compound X

Piperidine (20 μL) was added to a solution of Compound V (12 mg) in dimethylformamide (200 μL) and the solution was stirred at room temperature for 5 min. Volatile material was removed under a stream of nitrogen and chromatographed over a reverse phase HPLC (ZORBAX RX C-8, 22×250 mm, gradient of 20 to 70% aqueous $CH_3CN$ containing 0.1% TFA, flow rate 8 mL/min). The product eluted from 50 to 58 min. The combined fractions were directly lyophilized to yield colorless powder of trifluoroacetate salt of Compound X. $^1$H NMR ($CD_3CN$—$CDCl_3$, 1:1) δ: (only distinct signals are listed) 5.37 (1H, t, J=2 Hz, H-15), 5.05 (1H, dt, J=12, 4.5 Hz, H-2), 4.77 (1H, d, J=0.8 Hz, H-12), 4.63 (1H, d, J=10 Hz, H-3), 4.48 (1H, brs, H-28), 4.43(1H, d, J=1.2 Hz, H-28), 3.86 (1H,brs, H-11), 3.65 (4H, m, 2×gly-$CH_2$), 2.01 (1H, heptet, J=7.2 Hz, H-25), 1.81 (3H, s, $COCH_3$), 1.10 (3H, s, $CH_3$), 0.81 (3H, s, $CH_3$), 0.79, 0.78 (6H, d, J=7 Hz, $H_3$-26, $H_3$-27), 0.75 (3H, s, $CH_3$), 0.71 (3H, s, $CH_3$), 0.65 (3H, d, J=6.5 Hz, $H_3$-21), ESIMS m/z: 629 (M+H)$^+$, HREIMS (m/z): 628.4012 (calcd for $C_{36}H_{56}N_2O_7$: 628.4087).

EXAMPLE 18

Preparation of Glycine Esters Compound Y and Z

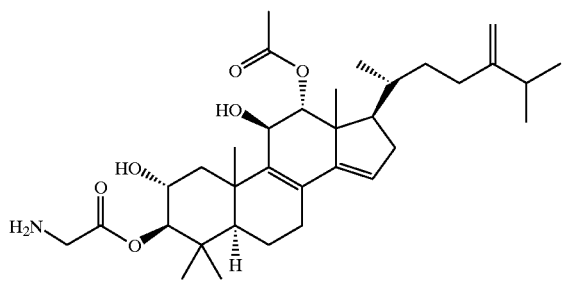

Compound Y

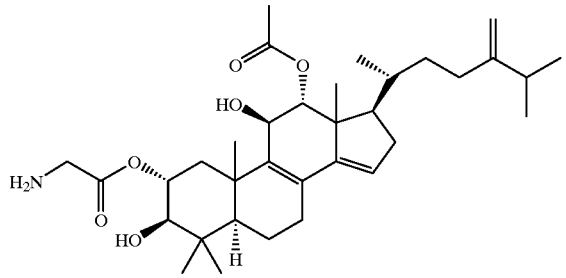

Compound Z

Compound W (8 mg) is reacted in DMF (100 μL) with piperidine (20 μL). The products are chromatographed and lyophilized in a manner similar to the procedure described above. Compound Y: $^1$H NMR ($CD_3CN$—$CDCl_3$, 1:1) δ: (only distinct signals are listed) 5.35 (1H,brs, H-15), 4.76 (1H, brs, H-12), 4.48 (1H, brs, H-28), 4.43 (1H, brs, H-28), 4.40 (1H, d, J=9.5 Hz, H-3), 3.97 (1H,brs, H-11), 3.66 (3H, m, H-2, gly-$CH_2$), 2.01 (1H, heptet, J=7.2 Hz, H-25), 1.76 (3H, s, $COCH_3$), 1.06 (3H, s, $CH_3$), 1.03 (3H, s, $CH_3$), 0.82 (3H, s, $CH_3$), 0.79, 0.78 (6H, d, J=7 Hz, $H_3$-26, $H_3$-27), 0.70 (3H, s, $CH_3$), 0.66 (3H, d, J=6.5 Hz, $H_3$-21), ESIMS m/z: 572 (M+H)$^+$.

EXAMPLE 19

IV Integrase Assay: Strand Transfer Catalyzed by Recombinant Integrase

Assays for the strand transfer activity of integrase were conducted according to Wolfe, A. L. et al., J. Virol. 70, 1424 (1996, hereby incorporated by reference for these purposes. Data for representative compounds of the present invention follow:

| Compound | $IC_{50}$ (μM) |
|---|---|
| A1 | 14 |
| A3 | 15 |
| J | 16 |
| K | 68 |
| X | 5 |

EXAMPLE 20

Oral Composition

As a specific embodiment of an oral composition of a compound of this invention, 50 mg of a compound of the present invention is formatted with sufficient finely divided lactose to provide a total amount of 580 to 590 mg to fill a size 0 hard gelatin capsule.

While the foregoing specification teaches the principles of the present invention, with examples provided for the purpose of illustration, it will be understood that the practice of the invention encompasses all of the usual variations, adoptions, or modifications, as come within the scope of the following claims and their equivalents.

What is claimed:
1. A compound of the formula I

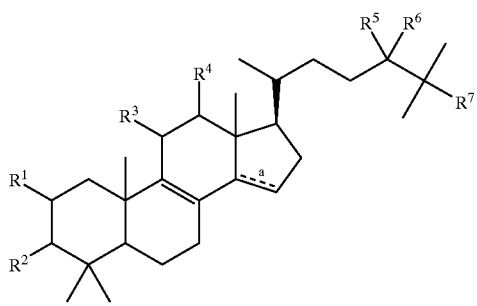

(I)

wherein:
"a" is selected from a single bond or a double bond;
$R^1$ is selected from:
(a) —OH,
(b) —OC(O)CH$_3$,
(c) —OC(O)CH$_2$C(CH$_3$)(OH)CH$_2$CO$_2$H,
(d) —OC(O)CH$_2$C(CH$_3$)(OH)CH$_2$CO$_2$CH$_3$,
(e) —OC(O)(CH$_2$)$_2$CO$_2$H,
(f) —OC(O)(CH$_2$)$_2$CO$_2$CH$_3$,
(g) —OC(O)(CH$_2$)$_2$CONHOH,
(h) —OCH$_2$OCH$_3$,
(i) —OC(O)C$_6$H$_5$,
(j) —OC(O)CH$_2$NH—C(O)OC(CH$_3$)$_3$,
(k) —OSO$_2$CH$_3$,
(l) —OC(O)CH$_2$NH$_2$, and
(m) —OC(O)—(CH$_2$)$_{15}$—OH;
$R^2$ is selected from:
(a) —OH,
(b) —OC(O)CH$_3$,
(c) =O,
(d) —OC(O)(CH$_2$)$_2$CO$_2$H,
(e) —OC(O)(CH$_2$)$_2$CO$_2$CH$_3$,
(f) —OC(O)(CH$_2$)$_2$CONHOH,
(g) —OCH$_2$OCH$_3$,
(h) —OC(O)C$_6$H$_5$,
(i) —OC(O)CH$_2$NHC(O)OC(CH$_3$)$_3$,
(j) —OSO$_2$CH$_3$,
(k) —OSO$_2$OH, and
(l) —OC(O)CH$_2$NH$_2$;
or $R^1$ and $R^2$ are joined to form:

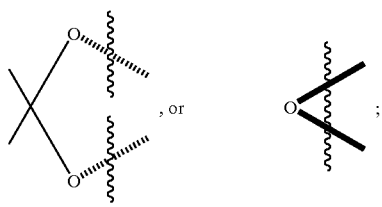

$R^3$ is selected from:
(a) —OH, and
(b) —OC(O)CH$_3$;
$R^4$ is selected from:
(a) —OH, and
(b) —OC(O)CH$_3$;
$R^5$ and $R^6$ are independently selected from:
(a) —H, and
(b) —OH,
or together form:
(c) =CH$_2$, or
(d) —CH$_2$O—;
$R^7$ is selected from:
(a) H, and
(b) OH;
or a pharmaceutically acceptable salt thereof;
provided that:
when
$R^1$ is —OH, —OC(O)—(CH$_2$)$_{15}$—OH, —OC(O)(CH$_2$)$_2$CO$_2$H, or —OC(O)CH$_3$, and
$R^2$ is —OH, —OSO$_2$OH, —OC(O)CH$_3$, or —OC(O)(CH$_2$)$_2$CO$_2$H, and
$R^3$ is —OH or —OC(O)CH$_3$, and
$R^4$ is —OH or —OC(O)CH$_3$,
then
$R^5$ and $R^6$ do not together form
(a) =CH$_2$, or
(b) —CH$_2$O—.

2. The compound according to claim 1,
wherein:
$R^1$ is selected from:
(a) —OH,
(b) —OC(O)CH$_3$,
(c) —OC(O)CH$_2$C(CH$_3$)(OH)CH$_2$CO$_2$H,
(d) —OC(O)CH$_2$C(CH$_3$)(OH)CH$_2$CO$_2$CH$_3$,
(e) —OC(O)(CH$_2$)$_2$CO$_2$H,
(f) —OC(O)(CH$_2$)$_2$CO$_2$CH$_3$,
(g) —OC(O)(CH$_2$)$_2$CONHOH,
(h) —OCH$_2$OCH$_3$,
(i) —OC(O)C$_6$H$_5$,
(h) —OC(O)CH$_2$NH—C(O)OC(CH$_3$)$_3$,
(k) —OSO$_2$CH$_3$,
(l) —OC(O)CH$_2$NH$_2$, and
(m) —OC(O)—(CH$_2$)$_{15}$—OH;
$R^2$ is selected from:
(a) —OH,
(b) —OC(O)CH$_3$,
(c) =O,
(d) —OC(O)(CH$_2$)$_2$CO$_2$H,
(e) —OC(O)(CH$_2$)$_2$CO$_2$CH$_3$,
(f) —OCH$_2$OCH$_3$,
(g) —OC(O)C$_6$H$_5$,
(h) —OC(O)CH$_2$NHC(O)OC(CH$_3$)$_3$,
(i) —OSO$_2$OH, and
(j) —OC(O)CH$_2$NH$_2$;
$R^3$ is —OH;
$R^4$ is —OC(O)CH$_3$;
$R^5$ and $R^6$ are independently selected from:
(a) —H, and
(b) —OH,
or together form:
(c) =CH$_2$, or
(d) —CH$_2$O—;
$R^7$ is H;
or a pharmaceutically acceptable salt thereof;
provided that:
when
$R^1$ is —OH, —OC(O)—(CH$_2$)$_{15}$—OH, —OC(O)(CH$_2$)$_2$C$_2$H, or —OC(O)CH$_3$, and
$R^2$ is —OH, —OSO$_2$OH, —OC(O)CH$_3$, or —OC(O)(CH$_2$)$_2$CO$_2$H, then
$R^5$ and $R^6$ do not together form
(a) =CH$_2$, or (b) —CH₂O—.

3. The compound according to claim 2 wherein:

R¹ is selected from:
- (a) —OH,
- (b) —OC(O)CH₂C(CH₃)(OH)CH₂CO₂H,
- (c) —OC(O)CH₂C(CH₃)(OH)CH₂CO₂CH₃,
- (d) —OC(O)(CH₂)₂CO₂H,
- (e) —OC(O)(CH₂)₂CONHOH,
- (f) —OC(O)CH₂NH₂, and
- (g) —OC(O)—(CH₂)₁₅—OH;

R² is selected from:
- (a) —OH,
- (b) =O,
- (c) —OC(O)(CH₂)₂CO₂H,
- (d) —OSO₂OH, and
- (e) —OC(O)CH₂NH₂;

R⁵ and R⁶ are independently selected from:
- (a) —H, and
- (b) —OH, or together form:
- (c) =CH₂, or
- (d) —CH₂O—;

or a pharmaceutically acceptable salt thereof;

provided that:

when
  R¹ is —OH, —OC(O)—(CH₂)₁₅—OH, or —OC(O)(CH₂)₂CO₂H, and
  R² is —OH, —OSO₂OH, or —OC(O)(CH₂)₂CO₂H, then
  R⁵ and R⁶ do not together form
  (a) =CH₂, or
  (b) —CH₂O—.

4. A compound selected from:

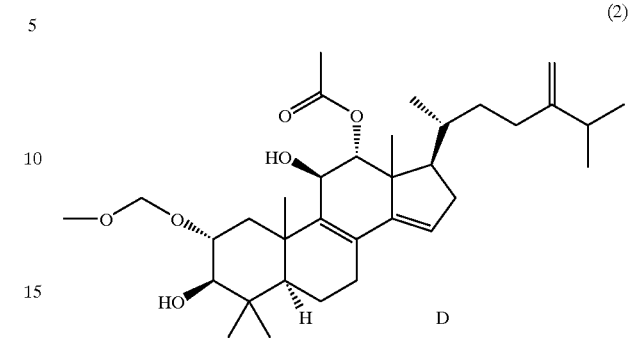

(2) D

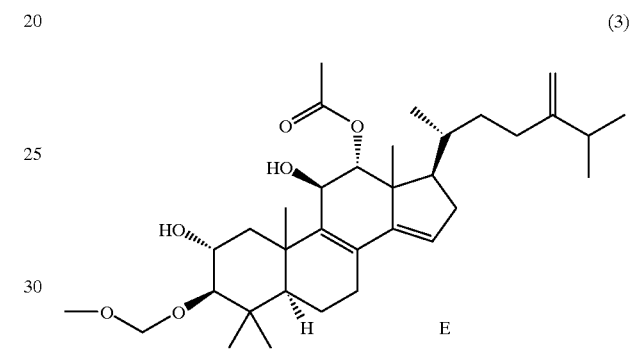

(3) E

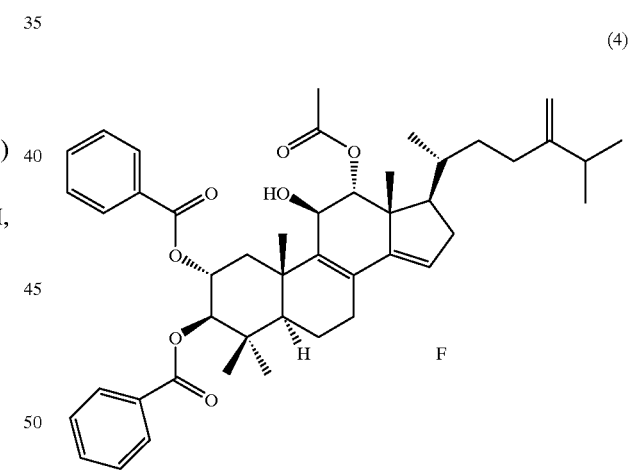

(4) F

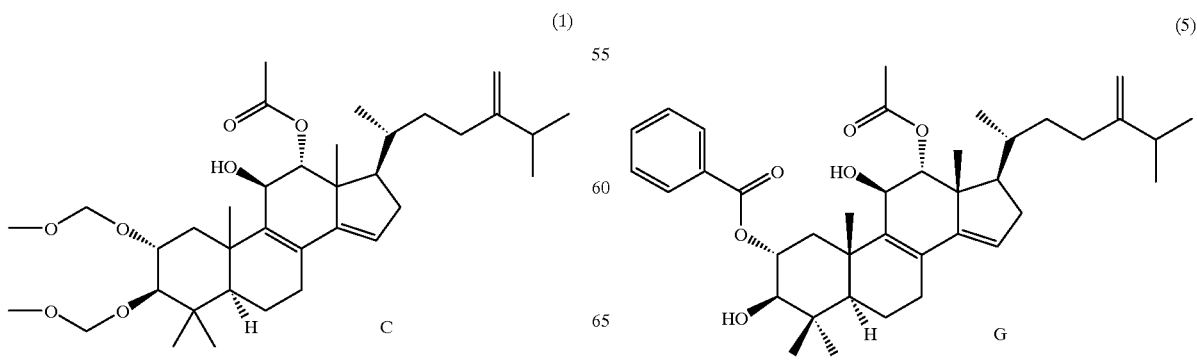

(1) C (5) G (6)
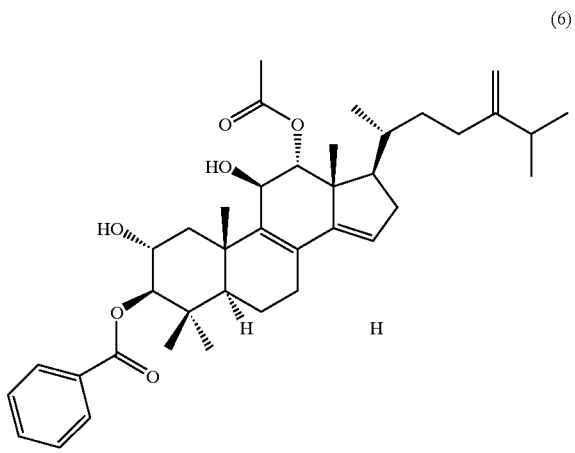
H
(10)
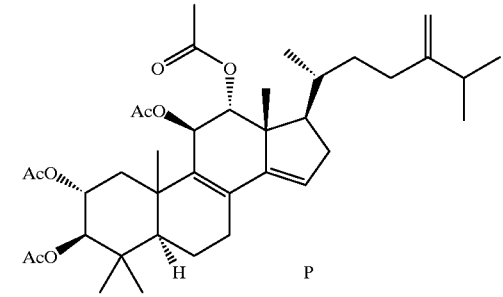
P
(7)
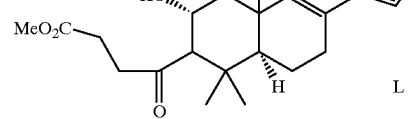
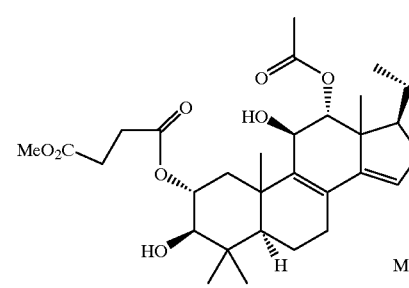
L
(11)
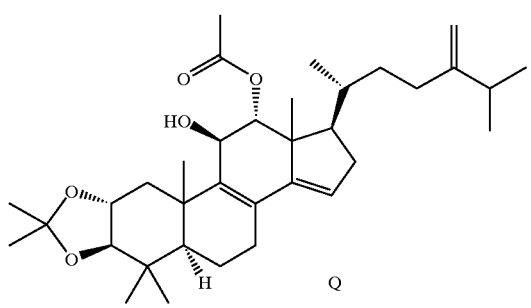
Q
(8)
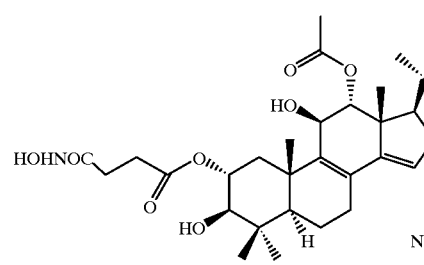
M
(12)
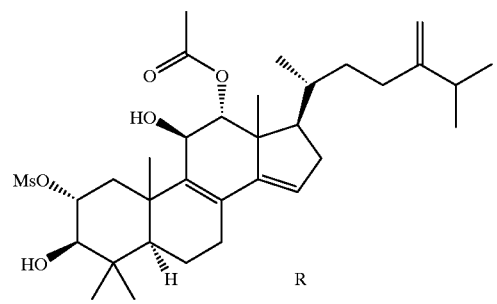
R
(9)
N
(13)
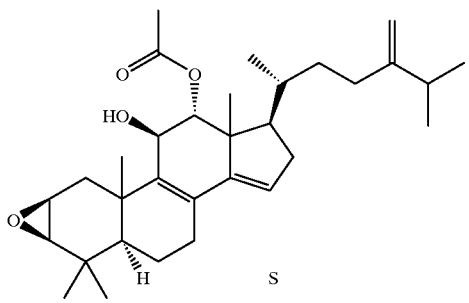
S -continued

(14) T

(15) U

(16) V

(17) W

(18) X

(19) Y ; and

(20) Z.

5. The compound according to claim 1 selected from:

(1)

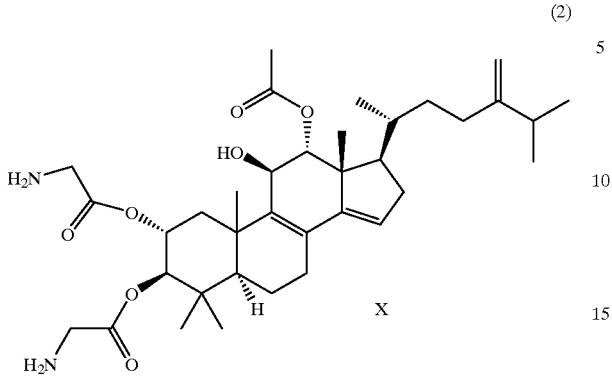
(2)

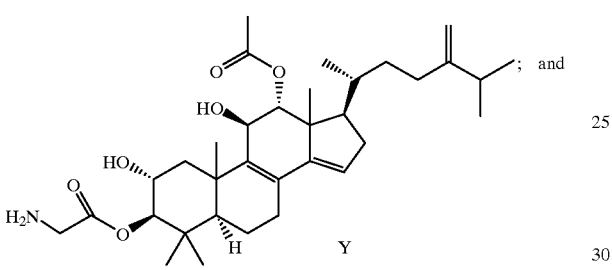
(3) ; and

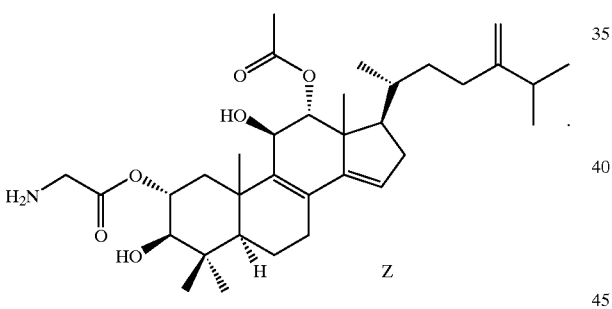
(4)

6. A pharmaceutical composition comprising a therapeutically effective amount of a compound according to claim 1, or a pharmaceutically acceptable salt thereof, and a pharmaceutically acceptable carrier.

7. The pharmaceutical composition of claim 6, further comprising a therapeutically effective amount of an AIDS treatment agent selected from:

(a) an AIDS antiviral agent, (b) an immunomodulator, and (c) an anti-infective agent.

8. A composition made by combining the compound of claim 1 and a pharmaceutically acceptable carrier.

9. A process for making a pharmaceutical composition comprising combining a compound of claim 1 and a pharmaceutically acceptable carrier.

10. A composition comprising a therapeutically effective amount of compound of structural formula I:

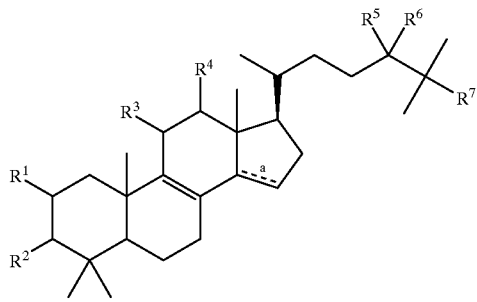
(I)

wherein:

"a" is selected from a single bond or a double bond;

$R^1$ is selected from:
(a) —OH,
(b) —OC(O)CH$_3$,
(c) —OC(O)CH$_2$C(CH$_3$)(OH)CH$_2$CO$_2$H,
(d) —OC(O)CH$_2$C(CH$_3$)(OH)CH$_2$CO$_2$CH$_3$,
(e) —OC(O)(CH$_2$)$_2$CO$_2$H,
(f) —OC(O)(CH$_2$)$_2$CO$_2$CH$_3$,
(g) —OC(O)(CH$_2$)$_2$CONHOH,
(h) —OCH$_2$OCH$_3$,
(i) —OC(O)C$_6$H$_5$,
(j) —OC(O)CH$_2$NH—C(O)OC(CH$_3$)$_3$,
(k) —OSO$_2$CH$_3$,
(l) —OC(O)CH$_2$NH$_2$,
(m) —OC(O)—(CH$_2$)$_{15}$—OH, and
(n) H;

$R^2$ is selected from:
(a) —OH,
(b) —OC(O)CH$_3$,
(c) =O,
(d) —OC(O)(CH$_2$)$_2$CO$_2$H,
(e) —OC(O)(CH$_2$)$_2$CO$_2$CH$_3$,
(f) —OC(O)(CH$_2$)$_2$CONHOH,
(g) —OCH$_2$OCH$_3$,
(h) —OC(O)C$_6$H$_5$,
(i) —OC(O)CH$_2$NHC(O)OC(CH$_3$)$_3$,
(j) —OSO$_2$CH$_3$,
(k) —OSO$_2$OH, and
(l) —OC(O)CH$_2$NH$_2$;

or $R^1$ and $R^2$ are joined to form:

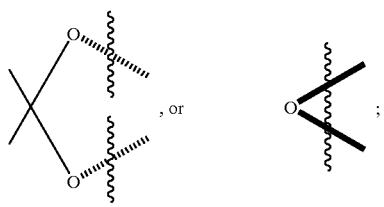

$R^3$ is selected from:
(a) —H,
(b) —OH, and
(c) —OC(O)CH$_3$;

$R^4$ is selected from:
(a) —H,
(b) —OH, and (c) —OC(O)CH$_3$;

R$^5$ and R$^6$ are independently selected from:
(a) —H,
(b) —OH, and
(c) —CH$_3$,
or together form:
(c) =CH$_2$, or
(d) —CH$_2$O—;

R$^7$ is selected from:
(a) H, and
(b) OH;

or a pharmaceutically acceptable salt thereof;
in combination with a therapeutically effective amount of an AIDS treatment agent selected from:
(a) an AIDS antiviral agent,
(b) an immunomodulator, and
(c) an anti-infective agent, and
a pharmaceutically acceptable carrier.

11. The composition according to claim 10 wherein the AIDS antiviral agent is: N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide, or a pharmaceutically acceptable salt thereof.

12. The composition according to claim 10, wherein the AIDS treatment agent is an AIDS antiviral agent which is an inhibitor of HIV protease, a non-nucleoside inhibitor of HIV reverse transcriptase, or a nucleoside inhibitor of HIV reverse transcriptase.

* * * * *